(12) United States Patent
Maiorano et al.

(10) Patent No.: US 12,342,992 B2
(45) Date of Patent: *Jul. 1, 2025

(54) INSTRUMENT PORT WITH FLUID FLUSH SYSTEM

(71) Applicant: The Children's Medical Center Corporation, Boston, MA (US)

(72) Inventors: Anthony Maiorano, Waltham, MA (US); Jeffrey C. Cerier, Franklin, MA (US)

(73) Assignee: The Children's Medical Center Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/706,279

(22) Filed: Mar. 28, 2022

(65) Prior Publication Data

US 2022/0354354 A1 Nov. 10, 2022

Related U.S. Application Data

(63) Continuation of application No. 15/916,844, filed on Mar. 9, 2018, now Pat. No. 11,284,788.

(51) Int. Cl.
*A61B 1/12* (2006.01)
*A61B 1/00* (2006.01)
(Continued)

(52) U.S. Cl.
CPC .......... *A61B 1/126* (2013.01); *A61B 1/00066* (2013.01); *A61B 1/00094* (2013.01);
(Continued)

(58) Field of Classification Search
CPC ............ A61B 1/00066; A61B 1/00068; A61B 1/00094; A61B 1/00101; A61B 1/00119;
(Continued)

(56) References Cited

U.S. PATENT DOCUMENTS 2,006,004 A 6/1935 Wenzel
2,243,992 A 6/1941 Charles
(Continued)

FOREIGN PATENT DOCUMENTS

EP 1426072 10/2008
EP 2433551 3/2012
(Continued)

OTHER PUBLICATIONS

Ahmed et al.; Initial clinical experience with a novel visualization and virtual electrode radiofrequency ablation catheter to treat atrial flutter, Heart Rhythm Society; 2011; pp. 361-367.
(Continued)

*Primary Examiner* — Aaron B Fairchild
*Assistant Examiner* — Stephen Floyd London
(74) *Attorney, Agent, or Firm* — Fish & Richardson P.C.

(57) ABSTRACT

In at least some aspects, an instrument port for introducing an instrument into a surgical site comprises: a port body having: an instrument channel extending through the port body; and a plurality of fluid flush channels each separate from one another and the instrument channel, each extending along a major portion of the port body and in fluid communication with the instrument channel; and a bulb comprising a bulb channel extending through the bulb, the bulb channel aligned with the instrument channel, wherein the bulb channel and instrument channel are configured to receive the instrument.

18 Claims, 20 Drawing Sheets

(51) Int. Cl.
 *A61B 1/015* (2006.01)
 *A61B 1/018* (2006.01)
 *A61B 1/05* (2006.01)
 *A61B 1/06* (2006.01)
 *A61B 17/00* (2006.01)
 *A61B 17/34* (2006.01)

(52) U.S. Cl.
 CPC ...... *A61B 1/00096* (2013.01); *A61B 1/00101* (2013.01); *A61B 1/00119* (2013.01); *A61B 1/00128* (2013.01); *A61B 1/015* (2013.01); *A61B 1/018* (2013.01); *A61B 17/3421* (2013.01); *A61B 17/3498* (2013.01); *A61B 1/05* (2013.01); *A61B 1/0676* (2013.01); *A61B 1/125* (2013.01); *A61B 2017/00243* (2013.01); *A61B 17/3415* (2013.01); *A61B 2017/3445* (2013.01); *A61B 2217/005* (2013.01); *A61B 2217/007* (2013.01)

(58) Field of Classification Search
 CPC ..... A61B 1/00128; A61B 1/015; A61B 1/018; A61B 1/05; A61B 1/0676; A61B 1/125; A61B 1/126; A61B 17/3415; A61B 17/3421; A61B 17/3498; A61B 2017/00243; A61B 2017/3445; A61B 2217/005; A61B 2217/007; A61B 1/00091; A61B 1/00137; A61B 1/303; A61B 2017/3449; A61B 2017/3441; A61M 25/0026; A61M 2025/0037; A61M 25/0028; A61M 25/0029; A61M 25/003; A61M 25/0031; A61M 2025/0032; A61M 2025/0034; A61M 2025/0035; A61M 2025/0036; A61M 2025/004; A61M 2039/0264; A61M 2039/027; A61M 2039/0273; A61M 2039/0276; A61M 2039/0279; A61M 2039/0288
 See application file for complete search history.

(56) References Cited

U.S. PATENT DOCUMENTS

| | | | |
|---|---|---|---|
| 2,767,705 A | 10/1956 | Moore | |
| 4,201,199 A | 5/1980 | Smith | |
| 4,233,982 A | 11/1980 | Bauer et al. | |
| 4,436,087 A | 3/1984 | Ouchi | |
| 4,535,773 A | 8/1985 | Yoon | |
| 5,025,778 A | 6/1991 | Silverstein et al. | |
| 5,217,001 A | 6/1993 | Nakao et al. | |
| 5,261,391 A | 11/1993 | Inoue | |
| 5,381,782 A * | 1/1995 | DeLaRama | A61B 1/0056 604/95.01 |
| 5,441,503 A | 8/1995 | Considine et al. | |
| 5,454,807 A | 10/1995 | Lennox et al. | |
| 5,632,782 A | 5/1997 | Carlough | |
| 5,660,175 A | 8/1997 | Dayal | |
| 5,797,960 A | 8/1998 | Stevens et al. | |
| 5,842,971 A | 12/1998 | Yoon | |
| 5,855,569 A | 1/1999 | Komi | |
| 5,899,915 A | 5/1999 | Saadat | |
| 5,928,218 A | 7/1999 | Gelbfish | |
| 5,941,815 A | 8/1999 | Chang | |
| 6,013,024 A * | 1/2000 | Mitsuda | A61B 1/12 600/149 |
| 6,033,426 A | 3/2000 | Kaji | |
| 6,129,713 A | 10/2000 | Mangosong et al. | |
| 6,178,346 B1 | 1/2001 | Amundson et al. | |
| 6,293,282 B1 | 9/2001 | Lemelson | |
| 6,309,345 B1 | 10/2001 | Stelzer et al. | |
| 6,315,714 B1 | 11/2001 | Akiba | |
| 6,503,192 B1 | 1/2003 | Ouchi | |
| 6,554,793 B1 | 4/2003 | Pauker et al. | |
| 6,612,304 B1 | 9/2003 | Cise et al. | |
| 6,641,562 B1 | 11/2003 | Peterson et al. | |
| 6,689,085 B1 | 2/2004 | Rubenstein et al. | |
| 6,749,559 B1 | 6/2004 | Kraas et al. | |
| 7,442,167 B2 | 10/2008 | Dunki-Jacobs et al. | |
| 7,537,562 B2 | 5/2009 | Takano | |
| 7,914,444 B2 | 3/2011 | Moriyama et al. | |
| 8,287,447 B2 | 10/2012 | Gasche et al. | |
| 8,394,015 B2 | 3/2013 | DiBiasio et al. | |
| 8,425,407 B2 | 4/2013 | Sato et al. | |
| 8,430,811 B2 | 4/2013 | Hess et al. | |
| 8,491,631 B2 | 7/2013 | Del Nido et al. | |
| 8,926,502 B2 | 1/2015 | Levy et al. | |
| 8,951,275 B2 | 2/2015 | Cannon et al. | |
| 9,451,875 B2 | 9/2016 | Sigmon et al. | |
| 9,459,442 B2 | 10/2016 | Miller | |
| 9,709,795 B2 | 7/2017 | Miller | |
| 11,284,788 B2 | 3/2022 | Maiorano et al. | |
| 2002/0026094 A1 | 2/2002 | Roth | |
| 2002/0068853 A1 | 6/2002 | Adler | |
| 2002/0078963 A1* | 6/2002 | Rouns | A61M 16/0463 128/200.26 |
| 2002/0111585 A1 | 8/2002 | Lafontaine et al. | |
| 2004/0024414 A1 | 2/2004 | Downing | |
| 2004/0111019 A1 | 6/2004 | Long | |
| 2004/0116897 A1 | 6/2004 | Aboul-Hosn | |
| 2004/0193191 A1 | 9/2004 | Starksen et al. | |
| 2005/0197530 A1 | 9/2005 | Wallace et al. | |
| 2005/0234296 A1 | 10/2005 | Saadat et al. | |
| 2005/0234298 A1 | 10/2005 | Kucklick et al. | |
| 2006/0047185 A1 | 3/2006 | Shener et al. | |
| 2006/0264708 A1 | 11/2006 | Horne | |
| 2007/0066869 A1 | 3/2007 | Hoffman | |
| 2007/0185380 A1* | 8/2007 | Kucklick | A61B 17/0218 600/156 |
| 2007/0197896 A1 | 8/2007 | Moll et al. | |
| 2009/0048486 A1 | 2/2009 | Surti | |
| 2009/0275893 A1 | 11/2009 | DiBiasio et al. | |
| 2009/0287151 A1 | 11/2009 | Resca | |
| 2010/0286475 A1* | 11/2010 | Robertson | A61B 1/00188 600/109 |
| 2011/0288372 A1 | 11/2011 | Petersen | |
| 2011/0295072 A1 | 12/2011 | Boulais et al. | |
| 2012/0209074 A1 | 8/2012 | Titus | |
| 2012/0226103 A1 | 9/2012 | Gunday et al. | |
| 2012/0232342 A1 | 9/2012 | Reydel | |
| 2013/0172674 A1 | 7/2013 | Kennedy et al. | |
| 2013/0245371 A1 | 9/2013 | Mourlas et al. | |
| 2013/0281779 A1 | 10/2013 | Robertson | |
| 2014/0213847 A1 | 7/2014 | Green et al. | |
| 2014/0213848 A1 | 7/2014 | Moskowitz et al. | |
| 2014/0221749 A1 | 8/2014 | Grant et al. | |
| 2015/0025311 A1* | 1/2015 | Kadan | A61B 17/3474 600/104 |
| 2015/0065795 A1 | 3/2015 | Titus | |
| 2015/0209073 A1* | 7/2015 | Ahn | A61B 1/00154 600/114 |
| 2015/0313633 A1 | 11/2015 | Gross et al. | |
| 2015/0359416 A1* | 12/2015 | Simchony | A61B 1/0055 600/110 |
| 2016/0000463 A1 | 1/2016 | DiBiasio et al. | |
| 2016/0183777 A1 | 6/2016 | Daher et al. | |
| 2016/0367120 A1 | 12/2016 | Dupont et al. | |
| 2017/0049415 A1 | 2/2017 | Tsuruta | |
| 2017/0119435 A1* | 5/2017 | Gross | A61B 1/05 |
| 2017/0231477 A1 | 8/2017 | Del Nido et al. | |
| 2018/0103836 A1 | 4/2018 | Bawaadam et al. | |
| 2019/0038115 A1 | 2/2019 | Decherf et al. | |
| 2019/0110662 A1 | 4/2019 | Obara et al. | |
| 2019/0125176 A1* | 5/2019 | Burt | A61B 17/34 |
| 2019/0262020 A1 | 8/2019 | Lee et al. | |
| 2019/0274531 A1 | 9/2019 | Maiorano et al. | |
| 2020/0201023 A1 | 6/2020 | Kishi | |

FOREIGN PATENT DOCUMENTS

| | | |
|---|---|---|
| WO | WO 1998/024501 | 6/1998 |
| WO | WO 1998/040016 | 10/1998 |

(56) References Cited

FOREIGN PATENT DOCUMENTS

| WO | WO 2005/051175 | 6/2005 |
|---|---|---|
| WO | WO 2004/112652 | 7/2005 |
| WO | WO 2007/081800 | 7/2007 |
| WO | WO 2011/047339 | 7/2011 |
| WO | WO 2016/205694 | 12/2016 |
| WO | WO 2017/139629 | 8/2017 |

OTHER PUBLICATIONS

Ataollahi et al., "Cardioscopic Tool-Delivery Instrument for Beating-Heart Surgery," IEEE ASME transactions on Mechatronics, vol. 21, No. 1, Feb. 2016, pp. 584-590.

Dupont; "Invention Disclosure—Cardioscopes"; May 21, 2015; 5pp.

EP European Patent Office, "Extended European Search Report", App. No. 17750861.1, Sep. 30, 2019, European Patent Office.

EP Extended European Search Report in European Application No. 16812547.4, dated Feb. 21, 2019, 8 pages.

EP Extended European Search Report issued in EP07716358.2 on Apr. 24, 2014.

Maollahi et al., "Cardioscopic Tool-Delivery Instrument for Beating-Heart Surgery," IEEE ASME Transactions on Mechatronics, 21(1):1-1 (abstract), Jan. 2015 [retrieved on Apr. 15, 2019]. Retrieved from the internet: <URL:https://www.researchgate.net/publication/283309805_Cardiosoopic_Tool-Delivery Instrumentfor Beating-Heart Surgery>.

Padala et al.; Transapical beating heart cardiosoopy technique for off-pump visualization of heart valves; The Journal of thoracic and Cardiovascular Surgery; vol. 144, No. 1; 2012; pp. 231-234.

PCT International Search Report & Written Opinion, PCT/US17/17446, May 5, 2017, 16 pages.

PCT International Search Report and Written Opinion in International Appln. No. PCT/US07/00270, dated Oct. 1, 2007.

PCT International Search Report and Written Opinion in International Appln. No. PCT/US17/017445, dated Jun. 6, 2017.

PCT International Search Report and Written Opinion in International Appln. No. PCT/US2016/038147, dated Sep. 8, 2016.

PCT International Search Report, PCT/US2018/021746, May 25, 2018.

Shiose et al.; "Cardioscopy-guided surgery: Intracardiac mitral and tricuspid valve repair under direct visualization in the beating heart"; The Journal of thoracic and Cardiovascular Surgery; vol. 142, No. 1; 2011; pp. 199-202.

Uchida; "Recent Advances in Percutaneous Cardioscopy"; Curr Cardiovasc Imaging Rep; May 12, 2011; pp. 317-327.

Vasilyev et al.; "A Novel Cardioport for Beating-Heart Image-Guided Intracardiac Surgery"; Children's Hospital Boston, Harvard Medical School, Boston, Massachusetts Institute of Wechnology, Cambridge, Massachusetts; International Society for Minimally Invasive Cardiothoracic Surgery (ISMICS); Jun. 3, 2009.

Vasilyev et al.; "A novel cardioport for beating-heart, image-guided intracardiac surgery" The Journal of thoracic and Cardiovascular Surgery; vol. 142, No. 6; Dec. 2011; pp. 1545-1551.

Vasilyev et al.; "Three-Dimensional Echo and Videocardioscopy-Guided Atrial Septal Defect Closure"; Annals of Thoracic Surgery; 2006; vol. 82; pp. 1322-1326.

EP Office Action in European Appln. No. 18909091.3, mailed on Aug. 5, 2024, 4 pages.

\* cited by examiner

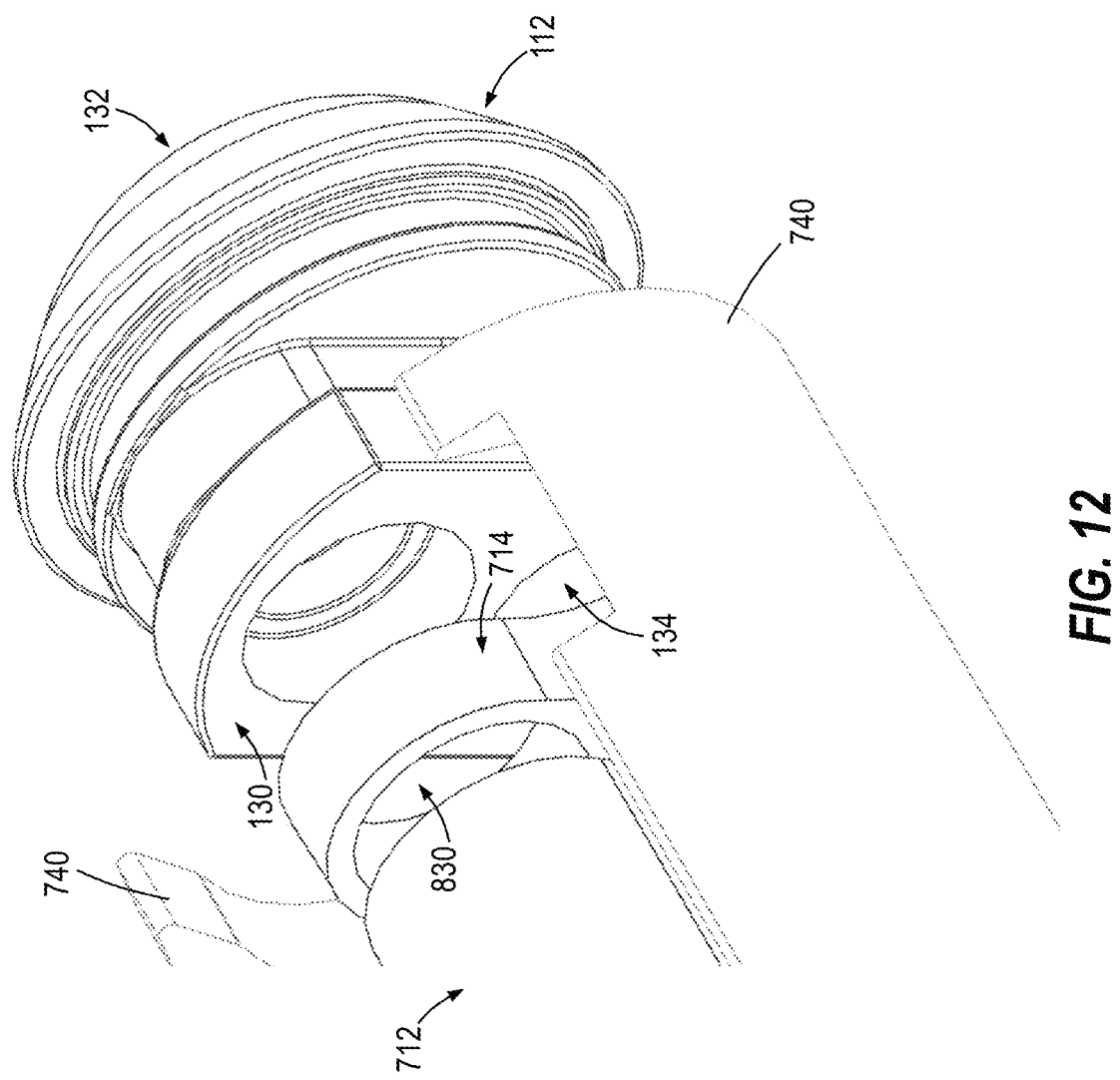

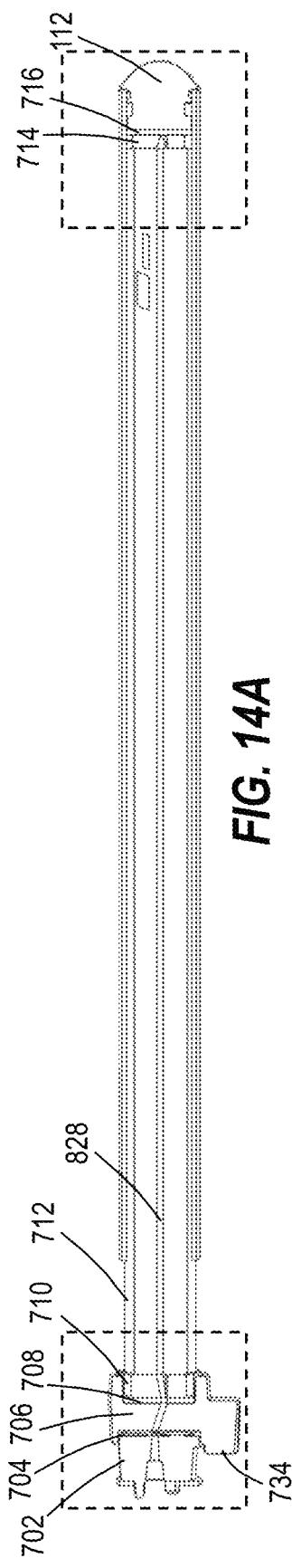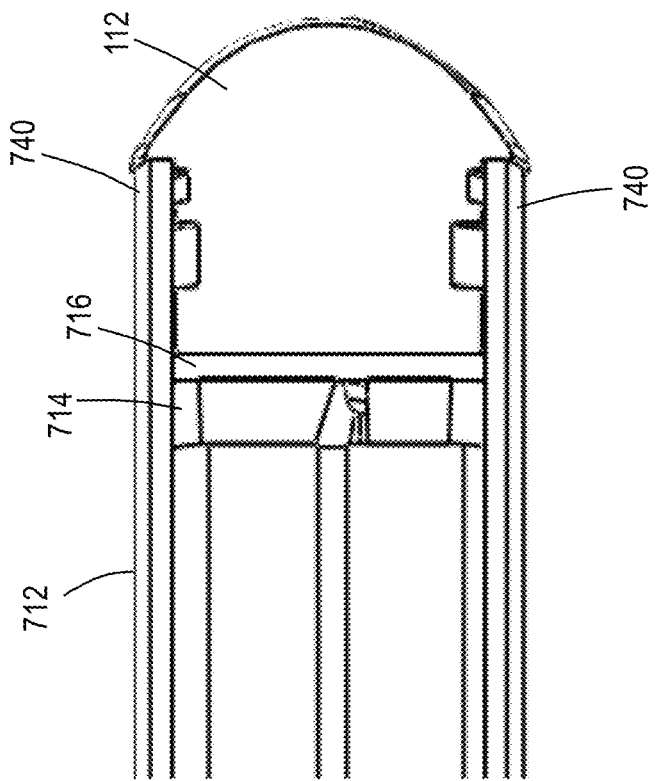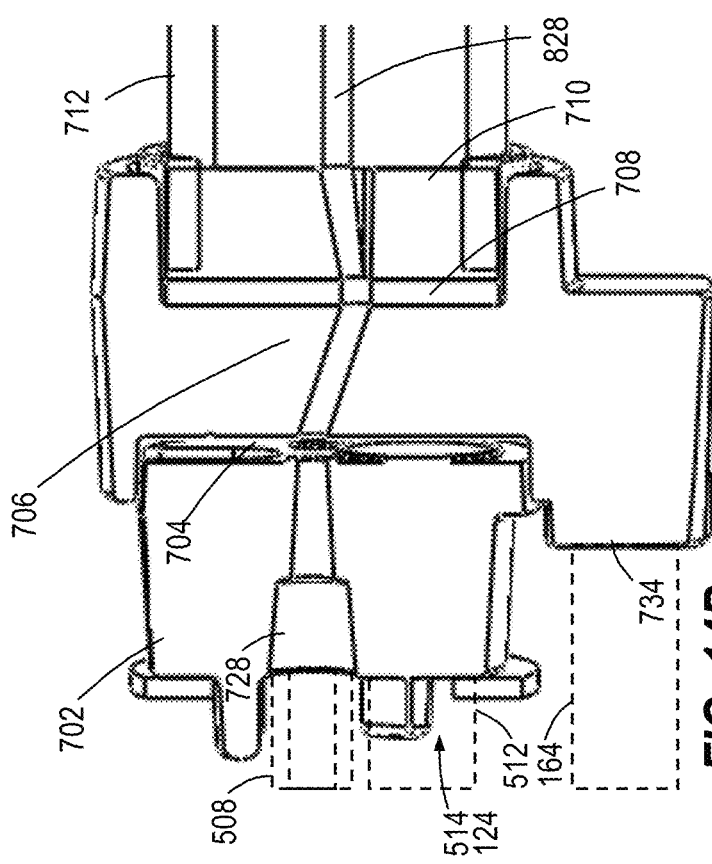
FIG. 14A
FIG. 14C
FIG. 14B

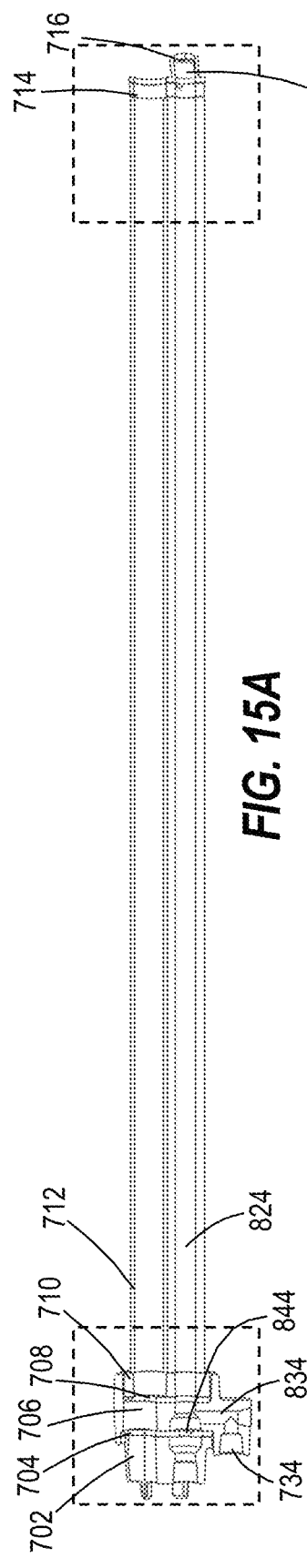
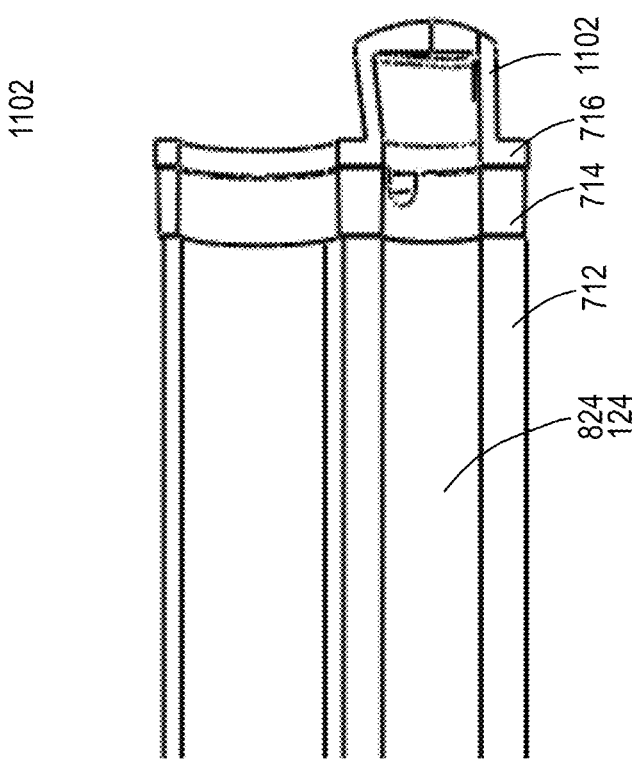
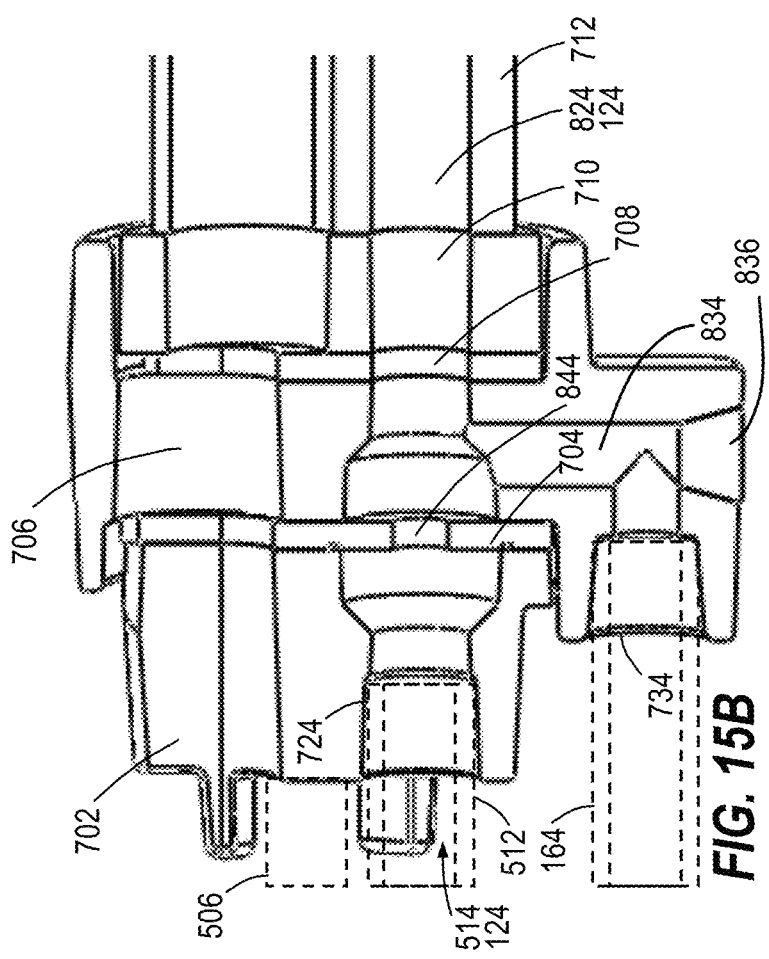
FIG. 15A
FIG. 15B
FIG. 15C

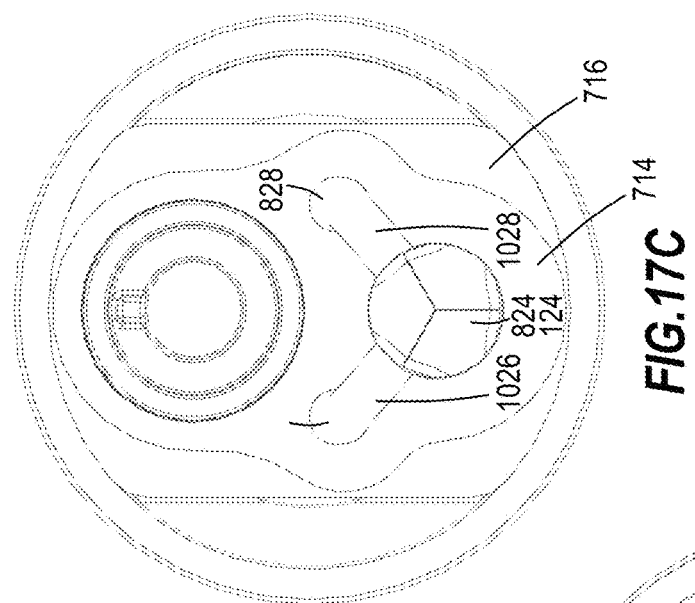
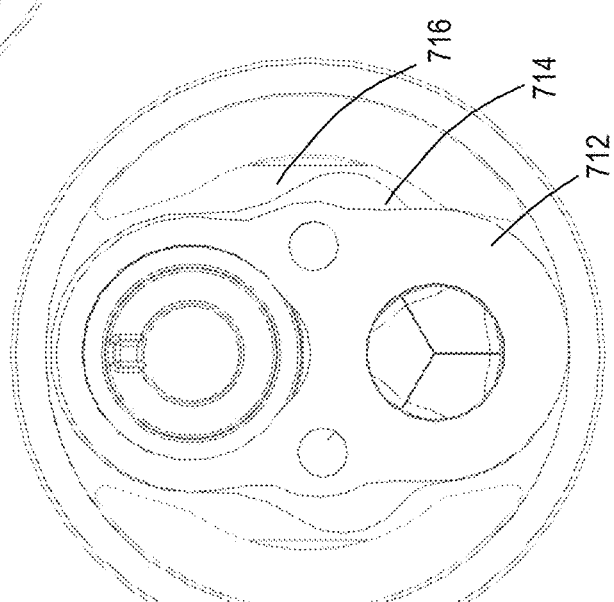
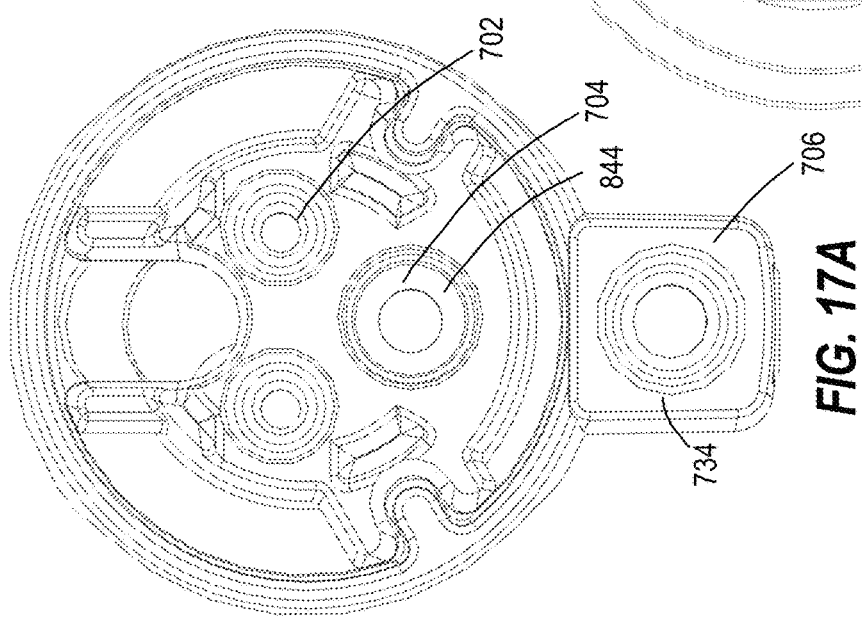

INSTRUMENT PORT WITH FLUID FLUSH SYSTEM

CROSS REFERENCE TO RELATED APPLICATION

This application is a continuation application of and claims priority to U.S. application Ser. No. 15/916,844, filed Mar. 9, 2018.

STATEMENT REGARDING FEDERALLY-SPONSORED RESEARCH

This invention was made with government support under Grant Number HL132655, awarded by the National Institutes of Health. The government has certain rights in the invention.

TECHNICAL FIELD

This application relates generally to devices and methods for minimally invasive image-guided surgery, such as, for example, but not limited to, cardiac surgery.

BACKGROUND

Instrument guides or ports can be used to guide the insertion of surgical instruments into a surgical site. Examples of procedures where such instruments ports or guides are used are beating-heart, minimally-invasive cardiac procedures to repair heart defects or to treat vascular heart disease. To position an instrument port at an appropriate location near the surgical site, current systems rely on either the operator's vision or a secondary optical system, such as an endoscope, that is inserted next to or into the instrument guide.

When an instrument port is inserted into a surgical site, it is exposed to body fluids such as for example, blood, saliva, or urine. Efforts are often taken to try to keep such bodily fluids from entering the instrument channel so as to reduce the possibility of contamination of the instrument channel, infection of the patient and/or damage to electronics or other sensitive components that may be in and/or in fluid communication with the instrument port. Efforts are also taken to try to keep air and/or other debris from entering the instrument channel so as to avoid the possibility of such air and/or other debris from entering the patient. Nonetheless, some bodily fluids, air and/or other debris may enter the instrument channel. To address this, some instrument ports include a flush system that allows the instrument channel of the instrument port to be flushed with fluid.

SUMMARY

It has been determined that, in at least some embodiments, flushing of an instrument channel may be enhanced, by providing one or more (e.g., a plurality of) fluid flush channels that are separate from the instrument channel and in fluid communication therewith, with less impact on a size (e.g., width) of the instrument port than would result if a single large flush channel is provided. In a preferred example, two fluid flush channels are provided.

In at least some aspects, an instrument port for introducing an instrument into a surgical site comprises: a port body having: an instrument channel extending through the port body; and a plurality of (e.g., two) flush channels each separate from one another and the instrument channel, each extending along a major portion of the port body and in fluid communication with the instrument channel; and a bulb comprising a bulb channel extending through the bulb, the bulb channel aligned with the instrument channel, wherein the bulb channel and instrument channel are configured to receive the instrument.

In at least some embodiments, the instrument port further comprises: a port connectable to a source of partial vacuum; and a valve in fluid communication between the port and the one or more, or plurality of flush channels, or between the port and the instrument channel, the valve having a normally closed state and including a button that is manually depressible or actuated to change the state of the valve from closed to open, the button releasable to allow the state to change from open to closed.

In at least some embodiments, the instrument port further comprises: a port connectable to a source of fluid; and a valve in fluid communication between the port and the instrument channel or between the port and a plurality of flush channels, the valve including a handle that is manually rotatable in a first direction to change a state of the valve from closed to open and manually rotatable in an opposite direction to return the state from open to closed.

In at least some embodiments, the instrument port includes the port that is connectable to the source of partial vacuum and the valve in fluid communication between the port and a plurality of flush channels (e.g., two channels), or between the port and the instrument channel, and further comprises: a second port connectable to a source of fluid; and a second valve in fluid communication between the second port and the instrument channel or between the second port and the plurality of flush channels, the second valve including a handle that is manually rotatable in a first direction to change a state of the second valve from closed to open and manually rotatable in an opposite direction to return the state from open to closed.

In at least some embodiments, each of the plurality of flush channels includes a major portion that is substantially parallel to a major portion of the instrument channel.

In at least some embodiments, the instrument port comprises a channel assembly having a plurality of sections that are assembled in a linear array and collectively define at least a portion of the instrument channel and the plurality of flush channels.

In at least some embodiments, the plurality of assembled sections includes: a port section, a first channel gasket, a channel and side port section, a second channel gasket and an elongated channel section that are assembled in a linear array and collectively define at least a portion of the instrument channel and the plurality of flush channels In at least some embodiments, the plurality of assembled sections further comprises: an adapter section disposed between the second channel gasket and the elongated channel section; and an adapter and manifold section disposed to a distal side of the elongated channel section.

In at least some embodiments, the plurality of assembled sections includes: a quad port section, a first quad channel gasket, a quad channel and side port section, a second quad channel gasket and an elongated quad channel section that are assembled in a linear array and collectively define at least a portion of the instrument channel and the plurality of flush channels.

In at least some embodiments, the plurality of assembled sections further comprises an adapter section disposed between the second quad channel gasket and the elongated quad channel section.

In at least some embodiments, the plurality of assembled sections further comprises an adapter and manifold section disposed to a distal side of the elongated quad channel section.

In at least some embodiments, the adapter and manifold section connects the plurality of flush channels to the instrument channel.

In at least some embodiments, the plurality of assembled sections further comprises: an adapter section disposed between the second quad channel gasket and the elongated quad channel section; and an adapter and manifold section disposed to a distal side of the elongated quad channel section.

In at least some embodiments, the elongated quad channel section comprises an elongated quad channel extrusion.

In at least some embodiments, the elongated quad channel section includes a manifold.

In at least some embodiments, the manifold connects the plurality of flush channels to the instrument channel.

In at least some embodiments, the elongated quad channel section includes a manifold at a distal end.

In at least some embodiments, the port body further includes an imaging system channel separate from the instrument channel and the plurality of flush channels and extending a major portion of the port body.

In at least some embodiments, a first one of the plurality of flush channels that is in fluid communication with the instrument channel and a second one of the plurality of flush channels that is in fluid communication with the instrument channel are disposed toward opposite sides of the channel assembly.

In at least some embodiments, the plurality of flush channels includes a first flush channel that is in fluid communication with the instrument channel and a second flush channel that is in fluid communication with the instrument channel, the channel assembly has a first side that extends along a major portion of the port body and a second side that is opposite the first side and extends along a major portion of the port body, a major portion of the first flush channel that is in fluid communication with the instrument channel is disposed toward the first side of the channel assembly, and a major portion of the second flush channel that is in fluid communication with the instrument channel is disposed toward the second side of the channel assembly that is opposite the first side of the channel assembly.

In at least some embodiments, the first one of the plurality of flush channels that is in fluid communication with the instrument channel and the second one of the plurality of flush channels that is in fluid communication with the instrument channel are disposed adjacent to opposite sides of the channel assembly.

In at least some embodiments, the plurality of flush channels includes a first flush channel that is in fluid communication with the instrument channel and a second flush channel that is in fluid communication with the instrument channel, the elongated channel section has a first side that extends along a major portion of the channel assembly and a second side that is opposite the first side and extends along a major portion of the channel assembly, a major portion of the first flush channel that is in fluid communication with the instrument channel is disposed adjacent to the first side of the elongated channel section, and a major portion of the second flush channel that is in fluid communication with the instrument channel is disposed adjacent to the second side of the elongated channel section that is opposite the first side of the elongated channel section.

In at least some embodiments, the instrument port comprises an imaging system.

In at least some embodiments, the imaging system comprises a camera and an illumination source, the illumination source configured to generate light having a first wavelength, wherein the bulb is at least partially optically transparent to the first wavelength of the light.

This Summary is intended to provide an overview of at least some of the subject matter of the present patent application. It is not intended to provide an exclusive or exhaustive explanation of the invention or embodiments thereof.

The following description and drawings set forth certain illustrative implementations of the disclosure in detail, which are indicative of several embodiments in which the various principles of the disclosure may be carried out. The illustrative embodiments, however, are not exhaustive of the many possible embodiments of the disclosure.

Thus, while certain aspects and embodiments have been presented and/or outlined in this Summary, it should be understood that the present aspects and embodiments are not limited to the aspects and embodiments in this Summary.

Other aspects and embodiments, which may be similar to and/or different from the aspects and embodiments presented in this Summary, will be apparent from the description, illustrations and/or claims, which follow.

In addition, while various features and/or advantages are described in this Summary, other features and/or advantages will be apparent from the following description, drawings and/or claims.

Any aspects and/or embodiments that are described in this Summary and do not appear in the claims that follow, are preserved for later presentation in this application or in one or more continuation patent applications. Any aspects and/or embodiments that are not described in this Summary and do not appear in the claims that follow, are also preserved for later presentation or in one or more continuation patent applications.

BRIEF DESCRIPTION OF THE DRAWINGS

FIG. 12 is an enlarged perspective view of a distal portion of the channel assembly, in a partly disassembled state, without the gasket and valve section, and an enlarged perspective view of the bulb, according to at least some embodiments;

FIG. 14A is a cross sectional view in a direction A-A shown in FIGS. 7 and 9A-9B, of a portion of the channel assembly and the bulb, according to at least some embodiments;

FIG. 14B is an enlarged cross section view in a direction A-A shown in FIGS. 7 and 9A-9B, of a proximal portion of the channel assembly and the bulb, according to at least some embodiments;

FIG. 14C is an enlarged cross section view in a direction A-A shown in FIGS. 7 and 9A-9B, of a distal portion of the channel assembly and the bulb, according to at least some embodiments;

FIG. 15A is a cross sectional view in a direction B-B shown in FIGS. 7 and 9A-9B, of a portion of the channel assembly and the bulb, according to at least some embodiments;

FIG. 15B is an enlarged cross section view in a direction B-B shown in FIGS. 7 and 9A-9B, of a proximal portion of the channel assembly and the bulb, according to at least some embodiments;

FIG. 15C is an enlarged cross section view in a direction B-B shown in FIGS. 7 and 9A-9B, of a distal portion of the channel assembly and the bulb, according to at least some embodiments;

FIG. 17A is an enlarged proximal end view of a portion of the channel assembly, according to at least some embodiments;

FIG. 17B is an enlarged proximal end view of a portion of the channel assembly, according to at least some embodiments;

FIG. 17C is an enlarged proximal end view of a portion of the channel assembly, according to at least some embodiments;

DETAILED DESCRIPTION

As stated above, when an instrument port is inserted into a surgical site, it is exposed to body fluids such as for example, blood, saliva, or urine. Efforts are often taken to try to keep such bodily fluids from entering the instrument channel so as to reduce the possibility of contamination of the instrument channel, infection of the patient and/or damage to electronics or other sensitive components that may be in and/or in fluid communication with the instrument port. Efforts are also taken to try to keep air and/or other debris from entering the instrument channel so as to avoid the possibility of such air and/or other debris from entering the patient. Nonetheless, some bodily fluids, air and/or other debris may enter the instrument channel. To address this, some instrument ports include a flush system that allows the instrument channel of the instrument port to be flushed with fluid.

As stated above, it has been determined that, in at least some embodiments, flushing of an instrument channel may be enhanced, by providing a plurality of flush channels that are separate from the instrument channel and in fluid communication therewith, with less impact on a size (e.g., width) of the instrument port than would result if a single large flush channel is provided.

Figure 1:
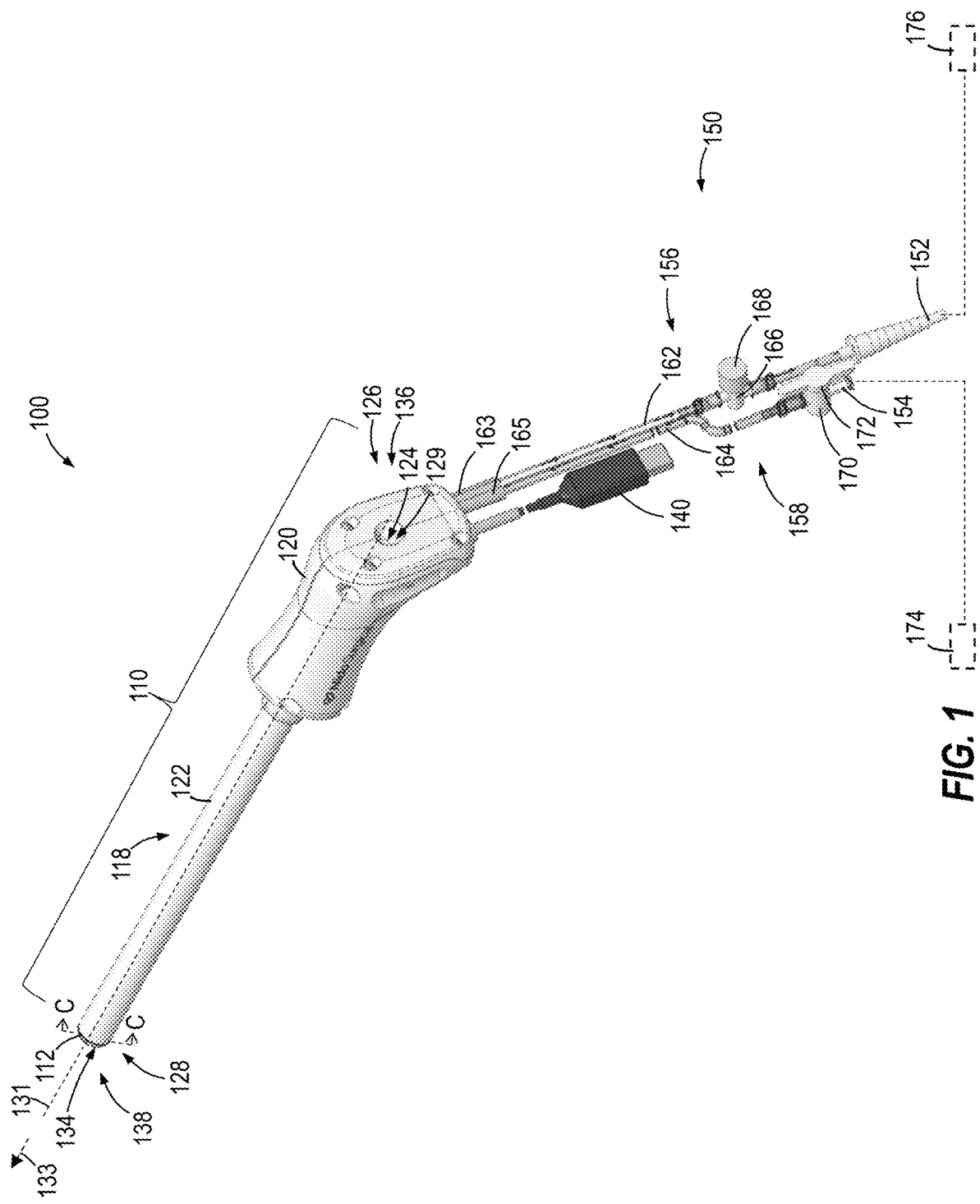
FIG. 1 is a perspective view of an instrument port for introducing one or more instruments into or near a surgical site of a patient, according to at least some embodiments.

FIG. 1 is a perspective view of an instrument port 100 that includes a plurality of flush channels, in accordance with at least some embodiments.

Figure 2:
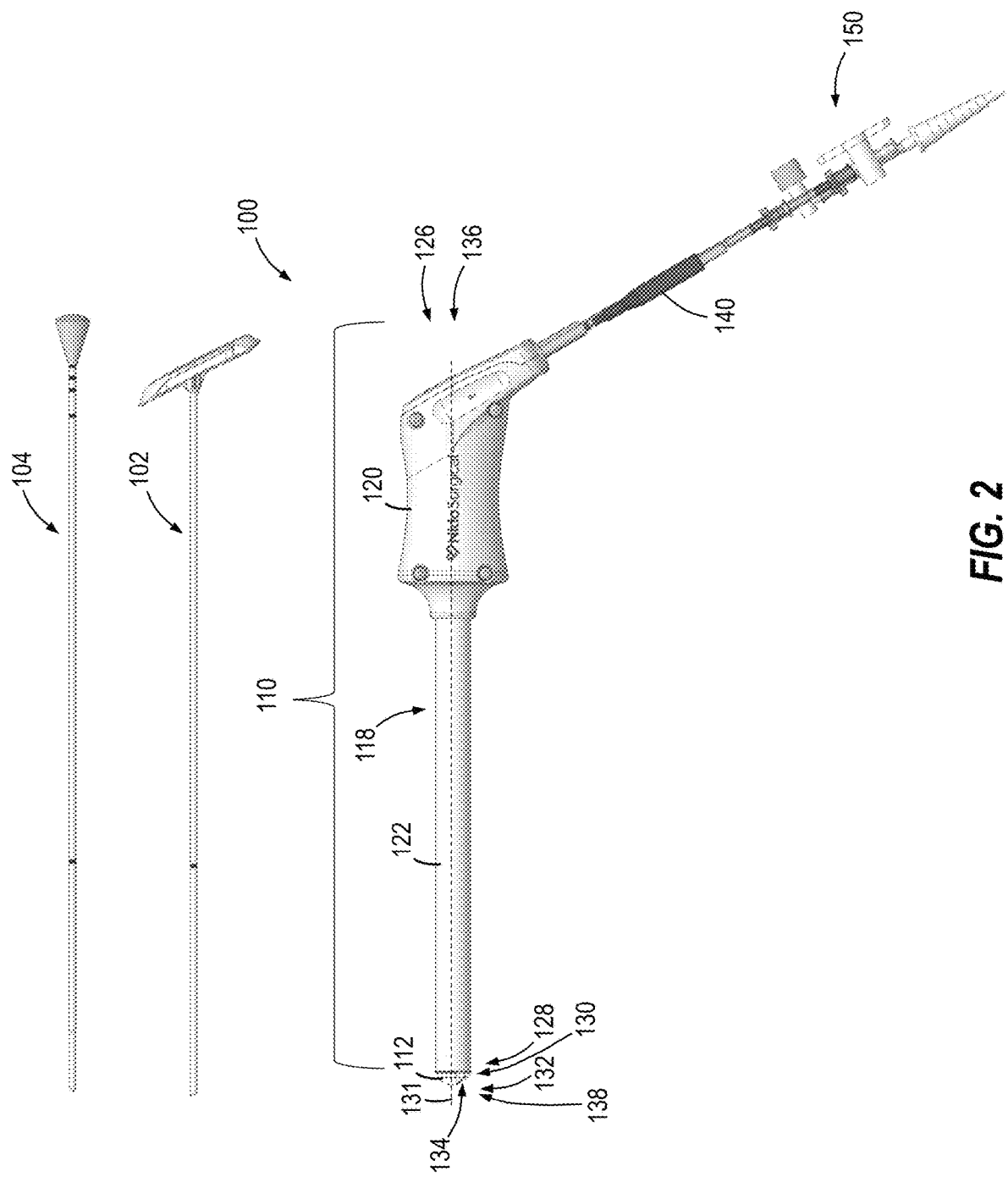
FIG. 2 is a side view of the instrument port and two instruments that may be guided by the instrument port, according to at least some embodiments.

FIG. 2 is a first side view of the instrument port 100 and a first side view of two (out of many different) types of instruments 102, 104 that may be guided by the instrument port, according to at least some embodiments.

Figure 3:
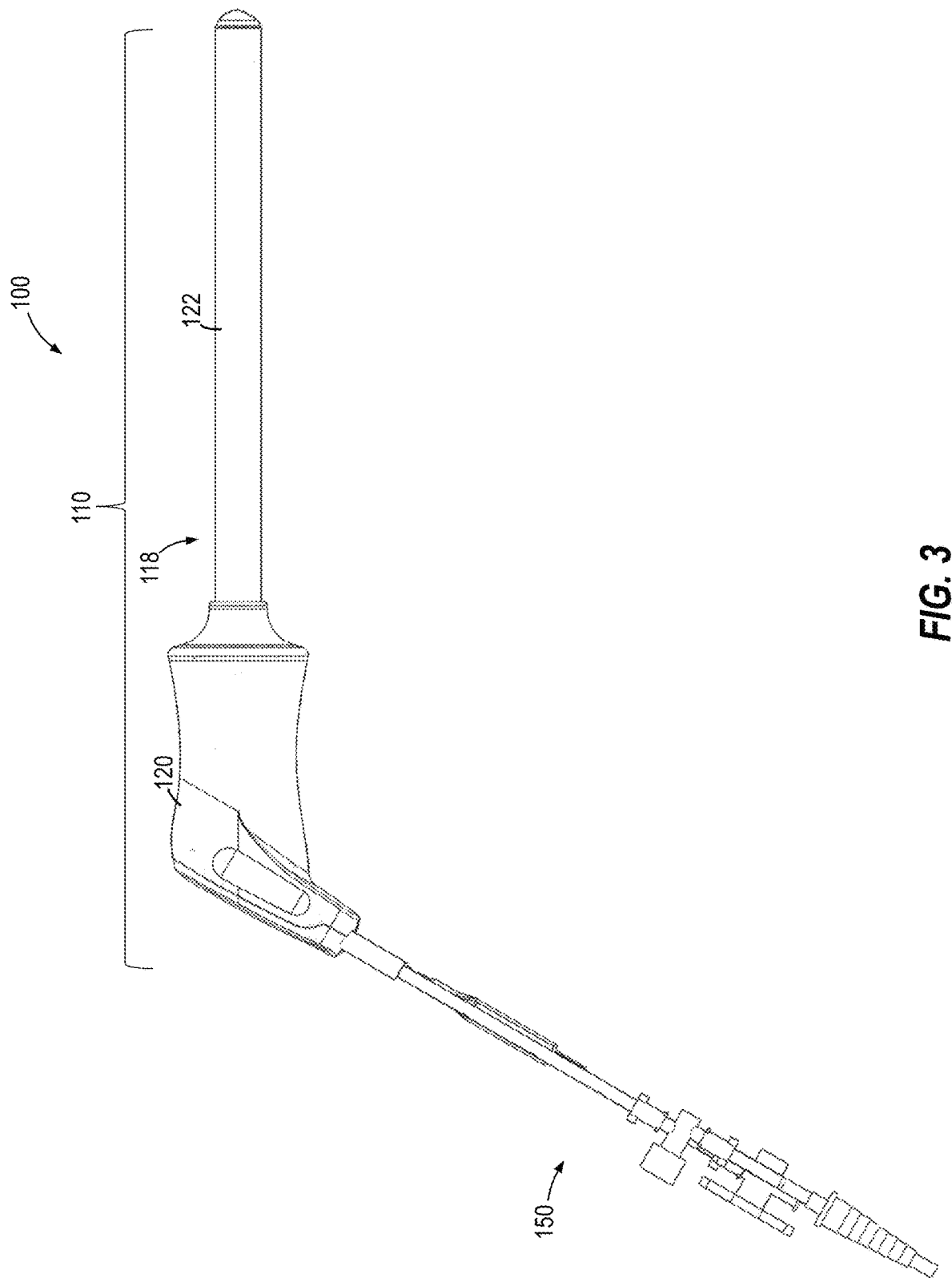
FIG. 3 is an opposite side view of the instrument port, according to at least some embodiments.

FIG. 3 is an opposite side view of the instrument port 100, according to at least some embodiments.

Referring now to FIGS. 1-3, in accordance with at least some embodiments, the instrument port 100 includes a port body 110, a bulb 112, and an imaging system, represented schematically by dashed rectangular box 114 (FIG. 4), which may be disposed within the bulb 112, at least in part. The port body 110 may include a housing 118 (which may have a handle 120 and a shaft 122) and may define a hollow instrument channel 124 that extends through the port body 110 (e.g., from a proximal end 126 of the port body 110 to a distal end 128 of the port body 110 or otherwise). The housing 118 may define a proximal portion 129 of the instrument channel 124.

The port body 110 may have a longitudinal axis 131, which may extend in a longitudinal direction 133. The shaft 122, which may have an elongated shape, may be disposed about and/or extend along the longitudinal axis 131 and/or in the longitudinal direction 133.

In at least some embodiments, the housing 118 and/or other portion(s) of the instrument port 100 may comprise a biocompatible material or materials that is/are appropriate for use in surgical applications, e.g., a medical grade polymer plastic, such as polycarbonate, polyvinyl chloride (PVC), polyvinylide fluoride, polypropylene, polyacetal, PolyEthylEthylKetone (PEEK), or another polymer; silicone; silicone rubber, and/or other material(s). In at least some embodiments, the housing 118 and/or other portion(s) of the instrument port 100 may comprise a rigid and/or durable material. In at least some embodiments, the housing 118 and/or other portion(s) of the instrument port 100 may comprise stainless steel, glass, PEEK, polycarbonate, and/or another durable material, which may be sterilized for re-use. In a preferred embodiment, the present apparatus is designed for a single-use and is therefore disposable after use on a given patient.

Figure 4:
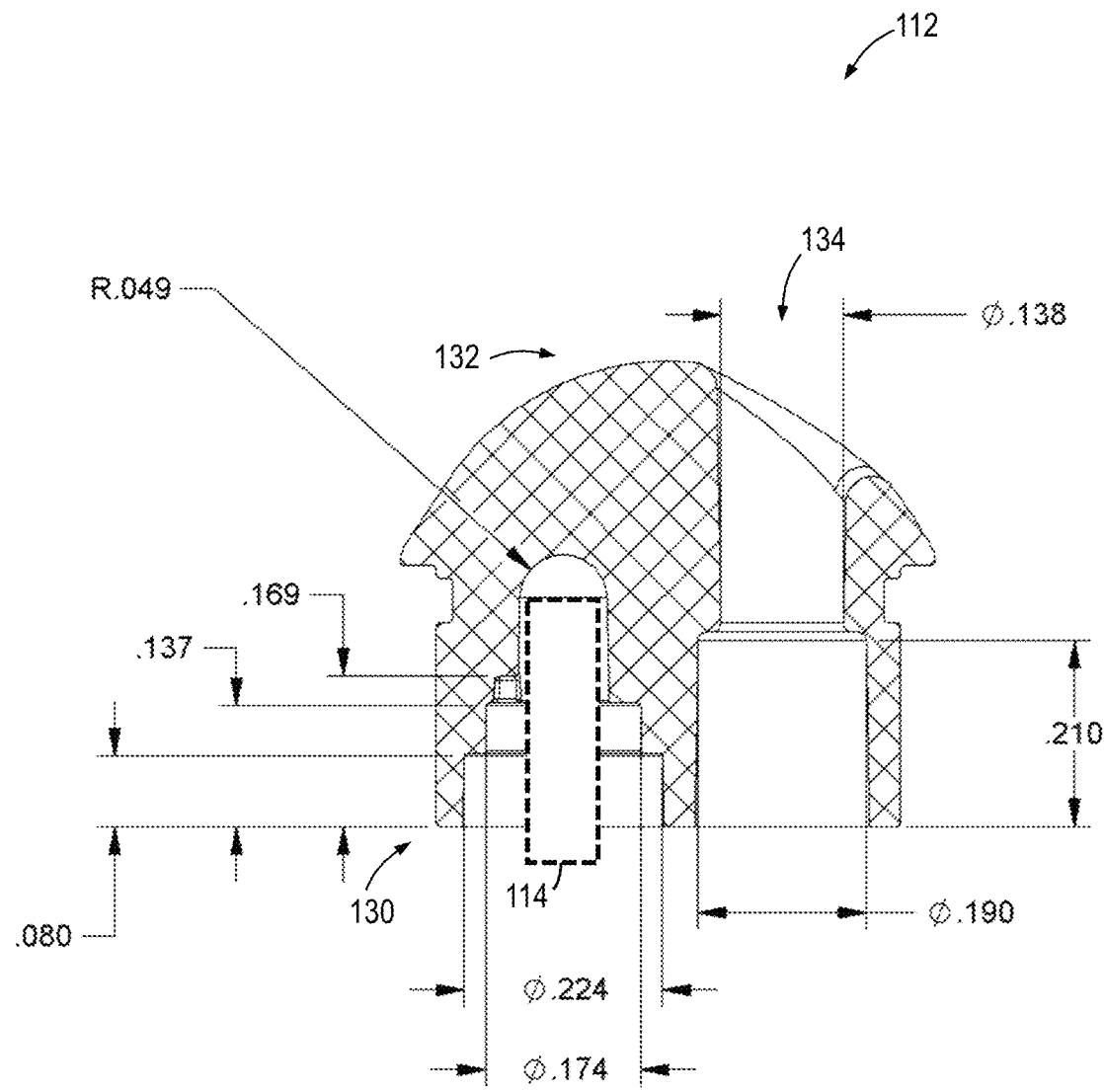
FIG. 4 is a cross section view in a direction C-C shown in FIG. 10f a bulb of the instrument port, according to at least some embodiments.

FIG. 4 is a cross section view in a direction C-C shown in FIG. 1 of one embodiment of the bulb 112, in accordance with at least some embodiments. Dimensions shown in FIG. 4 are expressed in inches. However, the bulb 112 is not limited to such configuration and/or dimensions.

Referring also now to FIG. 4, the bulb 112 may have a proximal end 130 and a distal end 132. The proximal end 130 of the bulb 112 may be disposed at or otherwise coupled to the distal end 128 of the port body 110.

The bulb 112 may define a hollow bulb channel 134 that extends through the bulb 112 (e.g., from the proximal end 130 (which may face the distal end 128 of the port body 110) to the distal end 132 or otherwise). The bulb channel 134 may be aligned or substantially aligned with a distal end of the instrument channel 124. Thus, the instrument channel 124 and bulb channel 134 may collectively define a continuous channel (or one or more portions of a continuous channel) from a proximal end 136 of the instrument port 100 to a distal end 138 of the instrument port 100.

The imaging system 114 may include a camera (e.g., a still or a video camera) and an illumination source, which may be disposed within the bulb 112, at least in part, at or near the distal end 138 of instrument port 100 and/or in any other suitable position(s). The imaging system 114 may be positioned and arranged so that the camera may acquire images of the distal opening 132 of the bulb channel 134 and/or the surgical site.

In at least some embodiments, the imaging system 114 may be disposed at the distal end 128 of the port body 110, in which case the bulb 112 may cover the imaging system 114 with a fluid-tight seal, which may cause the imaging system 114 to be fluidically isolated from external fluids, such as body fluids near a surgical site. Alternatively, the imaging system 114 may be disposed within or integrated into the bulb 112, for example encapsulated in a hollow region within the bulb 112, which fluidically isolates the imaging system 114. In another embodiment, the imaging system 114 may be disposed on a base, such as a post or pedestal, that extends from the distal end 128 of port body 110 into a hollow region defined in a proximal side of the bulb 112 to receive the imaging system. In at least some embodiments, the bulb 112 is attached to the port body 110 with a fluid-tight seal to fluidically isolate the imaging system 114 in the hollow region defined in the proximal side of bulb 112.

The imaging system 114 may include a USB or other connector 140, which may be coupled to the port body 110 and may include wires or other conductors that are electrically connected to the camera and/or the illumination source of the imaging system 114. The wires or other conductors may provide power that is supplied to the camera and/or illumination source and/or may transmit data that is collected by the camera to a computing device and/or display screen.

The instrument port 100 further includes a flush system 150 that may be used in flushing of emboli and/or debris (dust or other contaminants) from the instrument channel 124 and the bulb channel 134. Removing emboli and debris helps to prevent air bubbles and foreign material from entering the surgical site during use of the instrument port 100. For example, prior to heart surgery, the flush system may remove emboli and debris from entering the patient's heart during use of the instrument port 100, thus helping to avoid an embolism.

The flush system 150 may include a plurality of fluid ports, e.g., fluid ports 152 and 154, each of which may be coupled to the port body 110.

In the illustrated embodiment, the fluid port 152 is coupled to the instrument port 100 via a fluid line 156, which may comprise flexible, semi-flexible and/or rigid tubing 162 and/or any other type of fluid line (referred to hereinafter as fluid line 162). The fluid line 156 may extend through a sleeve 163 that is mounted or otherwise coupled to the port body 110, thereby coupling the fluid line 156 and the fluid port 152 to the port body 110. The fluid port 154 may be coupled to the instrument port 100 via a fluid line 158, which may comprise flexible, semi-flexible and/or rigid tubing 164 and/or any other type of fluid line (referred to herein as fluid line 164). The fluid line 158 may extend through a sleeve 165 that is mounted or otherwise coupled to the port body 110, thereby coupling the fluid line 158 and the fluid port 154 to the port body 110.

As used herein, the term "fluid line" means a line that has and/or receives fluid(s) (of any type(s), e.g., liquid and/or gas). It does not require that the line receive only fluid(s). Thus, a fluid line may receive debris.

In some other embodiments, one or more of the fluid ports, e.g., fluid ports 152, 154, may be mounted directly to the port body 110 or coupled to the port body 110 in any other manner(s). In at least some embodiments, one or more of the fluid ports, e.g., fluid ports 152, 154, may be integral with and/or defined by the port body 110.

One or more of the fluid lines, e.g., fluid lines 156, 158, may include a valve, which may be manually actuated, automatically actuated and/or a combination thereof. In the illustrated embodiment, the fluid line 156 includes a valve 166, which has a normally closed state and a button 168 that is manually depressible or actuated to change the state of the valve 166 from closed to open, sometimes referred to herein as a trumpet valve. Release of the button 168 allows the state of the valve 166 to return to the closed state. The fluid line 158 may include a valve 170, which may have a handle 172 that is manually rotatable in a first direction to change the state of the valve 170 from closed to open and manually rotatable in an opposite direction to return the state of the valve 170 to the closed state, sometimes referred to herein as a stopcock valve.

One of the fluid ports, e.g., fluid port 154, may comprise or may otherwise be employed as an inlet port and may be coupled to an external fluid reservoir 174 and/or other source of fluid (e.g., saline). The other of the fluid ports, e.g., fluid port 152, may comprise or may otherwise be employed as an outlet port and may be coupled to a suction source 176 and/or some other source of a partial vacuum. In the illustrated embodiment, the fluid port 154 is employed as the inlet port and is coupled to the external fluid reservoir 174; the fluid port 152 is employed as the outlet port and is coupled to the suction source 176.

As will be further described below with respect to FIGS. 5, 6, 7, 8, 9A-9B, 10, 11A-11B, 12 and 13, the flush system 150 may further include a plurality of flush channels that are separate from and in fluid communication with the instrument channel 124; a valve, which may be a one-way valve; and a seal.

Figure 5:
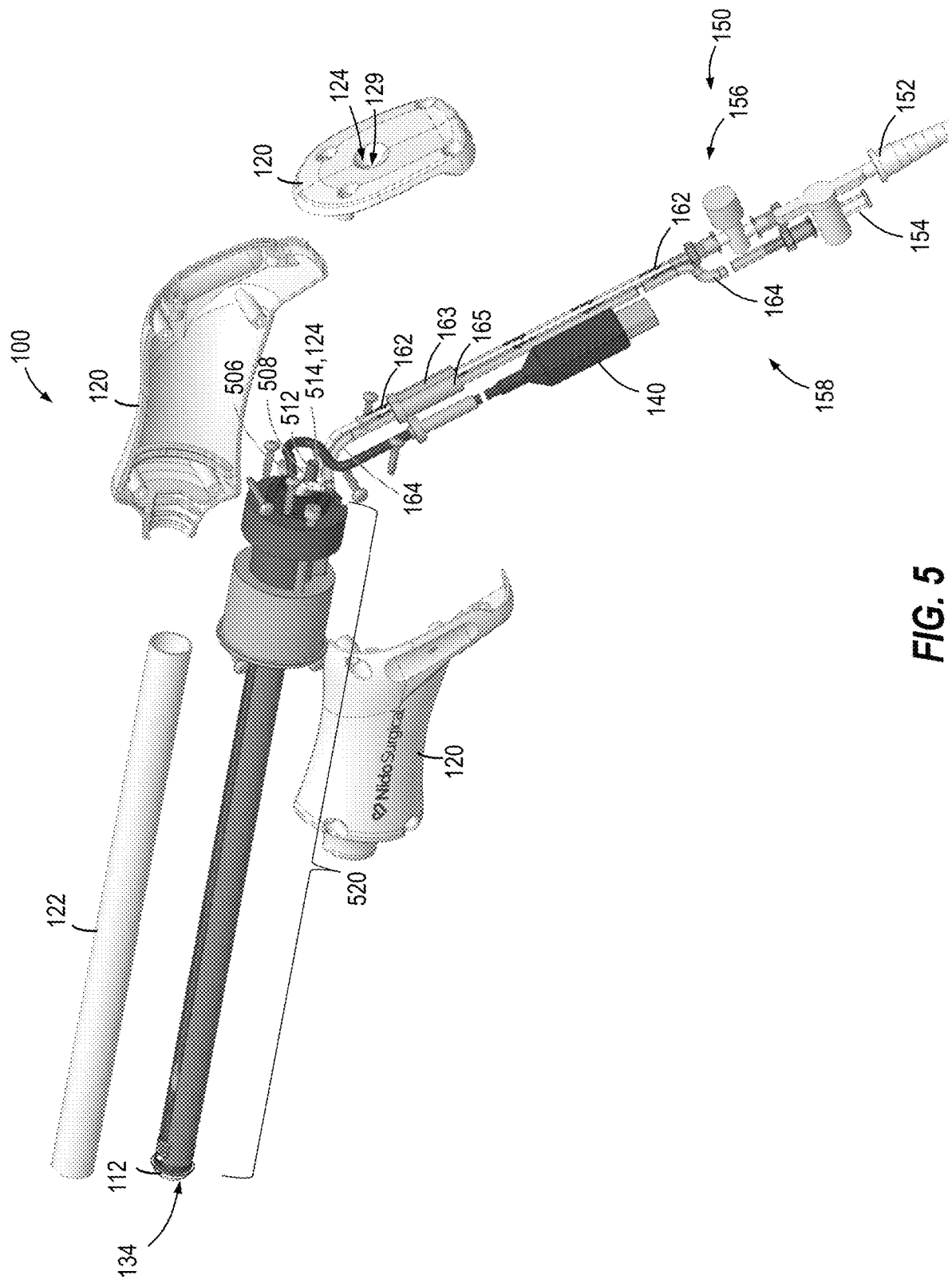
FIG. 5 is a perspective view of the instrument port, in a partly broken away, partly disassembled state, according to at least some embodiments.

FIG. 5 is a perspective view of the instrument port 100, in a partly broken away, partly disassembled state, according to at least some embodiments.

Figure 6:
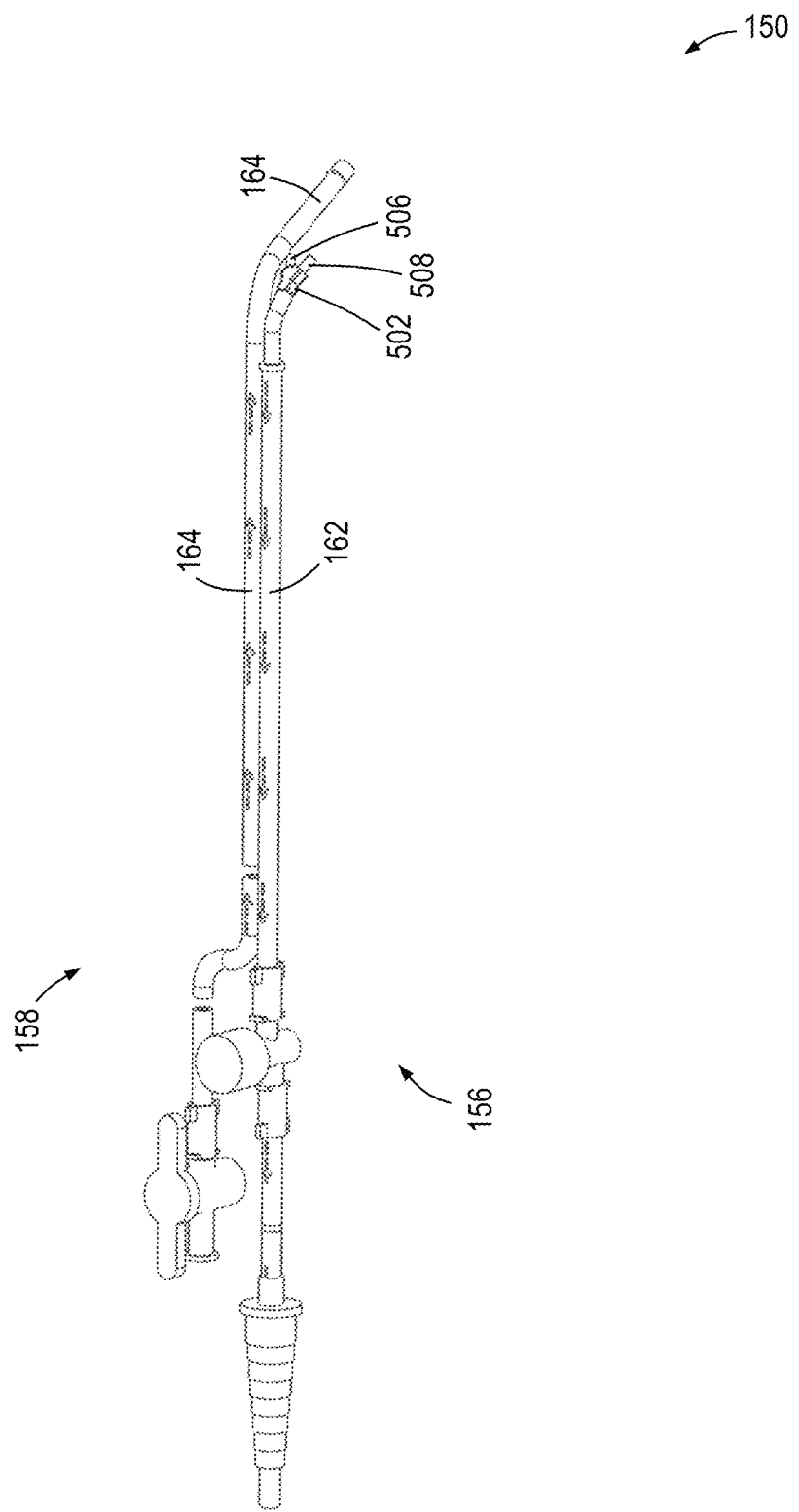
FIG. 6 is a perspective view of a portion of a flush system of the instrument port, in accordance with at least some embodiments.

FIG. 6 is a perspective view of a portion of the flush system 150, in accordance with at least some embodiments.

Referring also now to FIGS. 5-6, in accordance with at least some embodiments, the fluid line 156 of the flush system 150 may further include a tee or other type splitter 502 (FIG. 6) (which may or may not split equally), which may be coupled to and upstream of fluid line 162, to split the fluid line 156 into two fluid lines 506, 508. In the illustrated embodiment, the splitter 502 is disposed within the housing 118 and/or port body 110. In some other embodiments, the splitter 502 may be disposed outside the housing 118 and/or port body 110. In some other embodiments, instead of creating a second fluid line by splitting the fluid line 156 into the two fluid lines 506, 508, the instrument port 100 may include a second, separate fluid line (which may be similar to the fluid line 156) that is coupled to a source, e.g., source 176, independently of the fluid line 156. One potential disadvantage of adding a second fluid line similar to the fluid line 156, is that a second valve (i.e., a valve in the second fluid line) may be needed and may need to be actuated if fluid flow in the second fluid line similar to fluid line 156 is to be controlled.

The port body 110 may further include a tube 512 or other type of conduit that defines a channel 514 that serves as or otherwise constitutes a portion of the instrument channel 124. To facilitate such, the channel 514 may be aligned or substantially aligned with the proximal portion 129 of the instrument channel 124. In at least some embodiments, the channel 514 may be smaller in diameter than the proximal end of the instrument channel 124 so as to center or substantially center or otherwise help guide an instrument as it is inserted through the proximal end of the instrument channel 124.

The port body 110 may further include a channel assembly 520.

Figure 7:
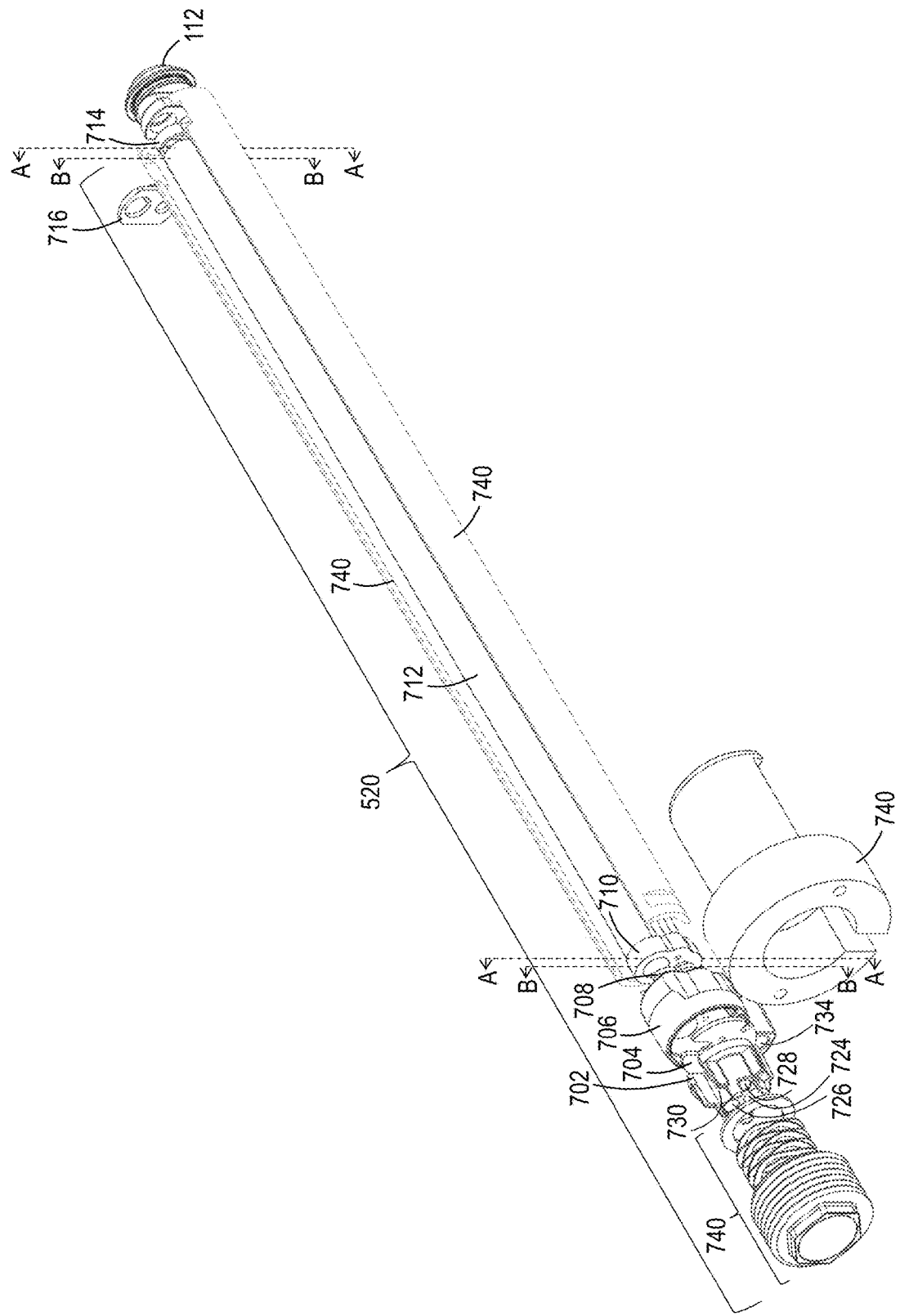
FIG. 7 is a perspective view of a channel assembly of the instrument port, in a partly broken away, partly disassembled state, and the bulb of the instrument port, according to at least some embodiments.

FIG. 7 is a perspective view of the channel assembly 520, in a partly broken away, partly disassembled state, and the bulb 112, according to at least some embodiments.

Referring also now to FIG. 7, in accordance with at least some embodiments, the channel assembly 520 may include a quad (or other quantity) port section 702, a quad (or other channel quantity) gasket 704, a quad (or other quantity) channel and side port section 706, a quad (or other channel quantity) channel gasket 708, a quad (or other quantity) channel adapter 710, an elongated quad (or other quantity) channel section 712, a quad (or other channel quantity) adapter and manifold section 714, and a gasket and valve section 716.

Unless stated otherwise, the term "section" means a segment or any other type of portion.

In at least some embodiments, the port section 702, the channel and side port section 706, the channel adapter 710, the elongated channel section 712, and the adapter and manifold section 714 may be rigid and/or may comprise polyvinyl chloride (PVC) and/or other rigid material(s).

It at least some embodiments, the gasket section 704, the gasket section 708, and the gasket and valve section 716 may be compliant and/or may comprise (or consist of) silicone (e.g., 70 A durometer silicone) and/or other compliant material(s).

The port section 702 may define a plurality of ports including: (i) an instrument channel port 724, (ii) a plurality of flush ports including a first flush port 726 and a second flush port 728 and (iii) an imaging system port 730. The instrument channel port 724 may receive a distal end of the tube 512 that defines the channel 514 that is a portion of the instrument channel 124. The flush port 726 may receive a distal end of the fluid line 506 of the flush system 150. The flush port 728 may receive a distal end of the fluid line 508 of the flush system 150. The imaging system port 730 may receive a camera of the imaging system 114, an illumination source (e.g., LEDs or the light guide) of the imaging system 114, one or more conductors that provide power to the camera and/or illumination source, and/or one or more conductors or other type of communication link that transmit data collected by the camera to a computing device and/or display screen.

The channel assembly 520 may further include a retainer assembly 740, which may provide or help to provide desired relative positioning between two or more of the sections in one or more lateral directions, and may further provide compression in a longitudinal direction to retain the sections of the channel assembly in the desired relative positioning.

The channel assembly 520 and flush system 150 are further described below with respect to FIGS. 8, 9A-9B, 10, 11A-11B, 12 and 13.

Figure 8:
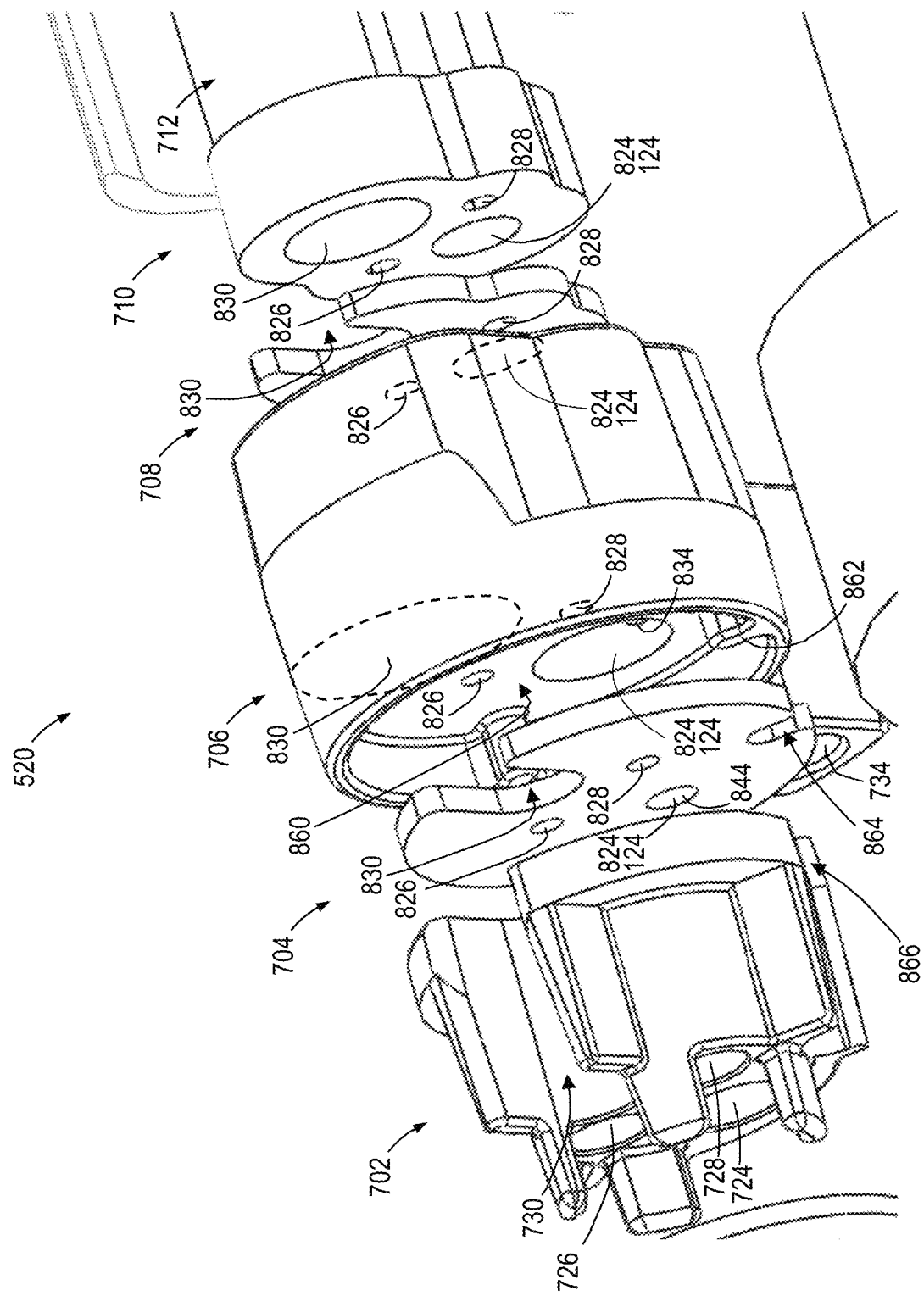
FIG. 8 is an enlarged perspective view of a proximal portion of the channel assembly, in a partly disassembled state, according to at least some embodiments.

FIG. 8 is an enlarged perspective view of a proximal portion of the channel assembly 520, in a partly disassembled state, according to at least some embodiments.

Figure 9:
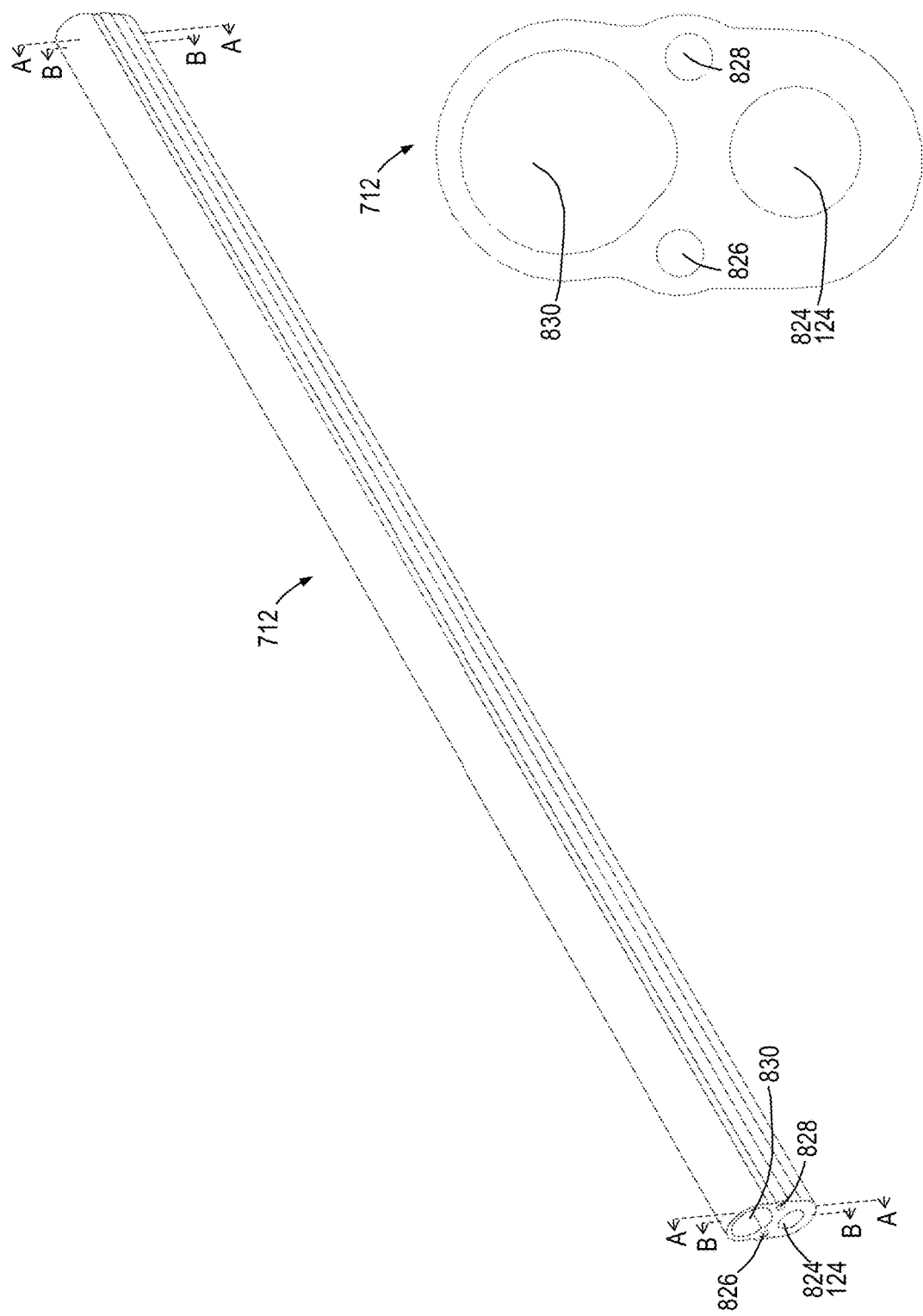
FIG. 9A is an enlarged perspective view of an elongated channel section, according to at least some embodiments.
FIG. 9B is an enlarged end view of the elongated channel section, according to at least some embodiments.

FIG. 9A is an enlarged perspective view of the elongated quad channel section 712, according to at least some embodiments.

FIG. 9B is an enlarged end view of the elongated quad channel section 712, according to at least some embodiments.

Figure 10:
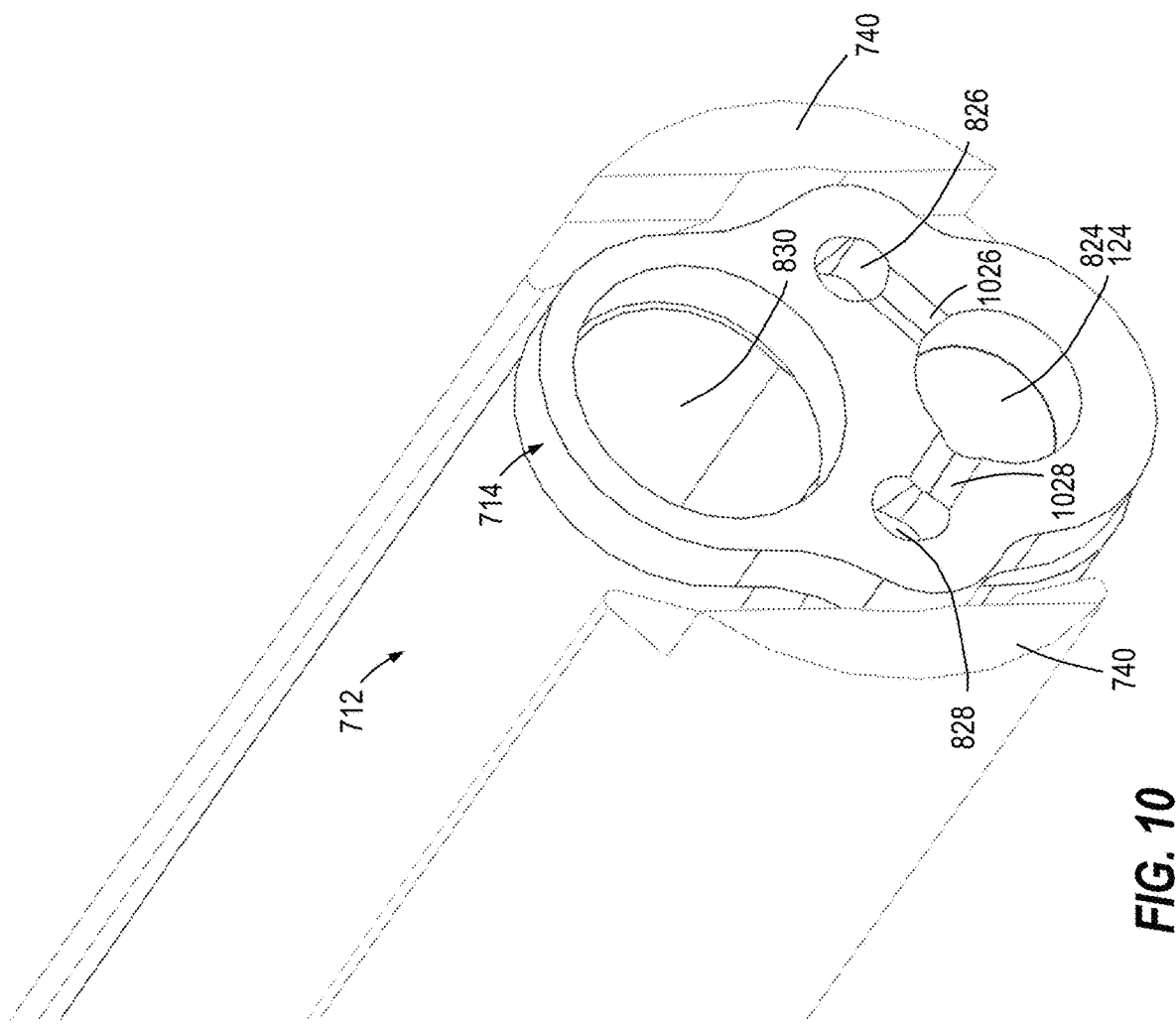
FIG. 10 is an enlarged perspective view of a distal portion of the channel assembly, in a partly disassembled state and without a gasket and valve section of the channel assembly, according to at least some embodiments.

FIG. 10 is an enlarged perspective view of a distal portion of the channel assembly 520, in a partly disassembled state and without the gasket and valve section 716, according to at least some embodiments.

Figure 11A:
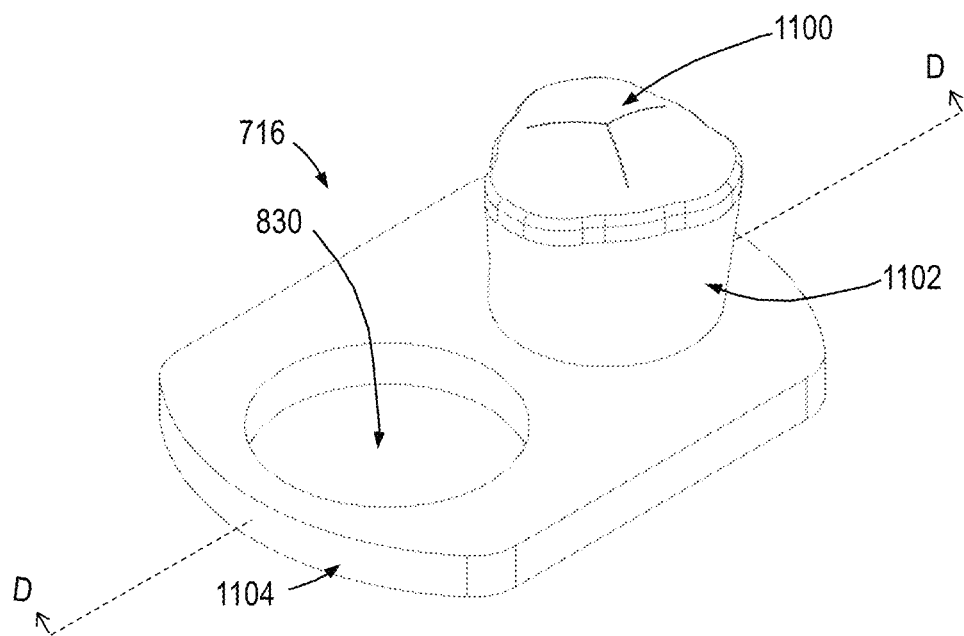
FIG. 11A is an enlarged perspective view in a direction D-D shown in FIG. 11A of a distal side of the gasket and valve section, according to at least some embodiments.

FIG. 11A is an enlarged perspective view of a distal side of the gasket and valve section 716, according to at least some embodiments.

Figure 11B:
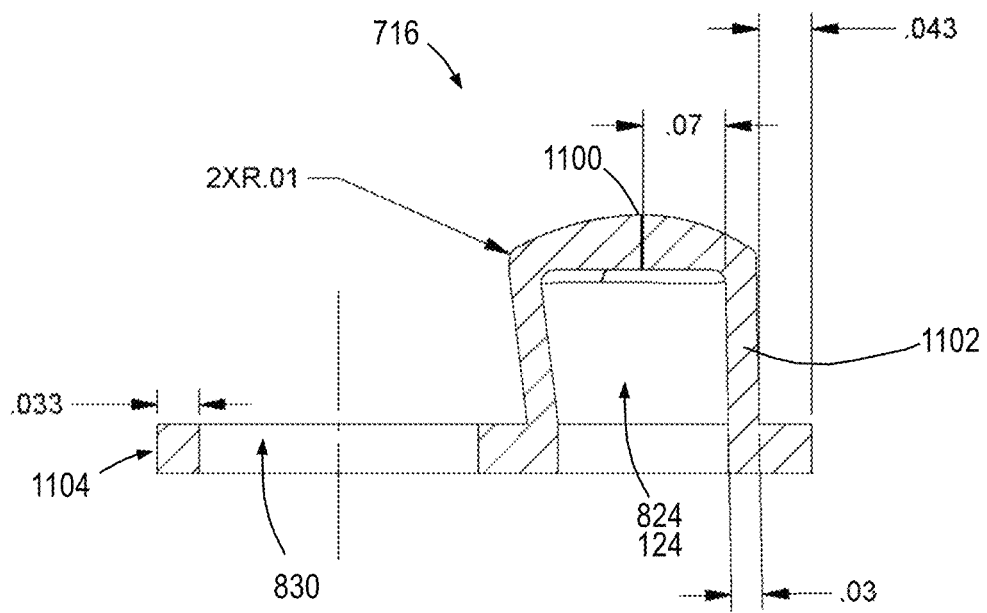
FIG. 11B is a cross sectional view of the gasket and valve section, according to at least some embodiments.

FIG. 11B is a cross sectional view in a direction D-D shown in FIG. 1A of the gasket and valve section 716, according to at least some embodiments.

FIG. 12 is an enlarged perspective view of a distal portion of the channel assembly 520, in a partly disassembled state, without the gasket and valve section 716, and an enlarged perspective view of the bulb 112, according to at least some embodiments.

Figure 13:
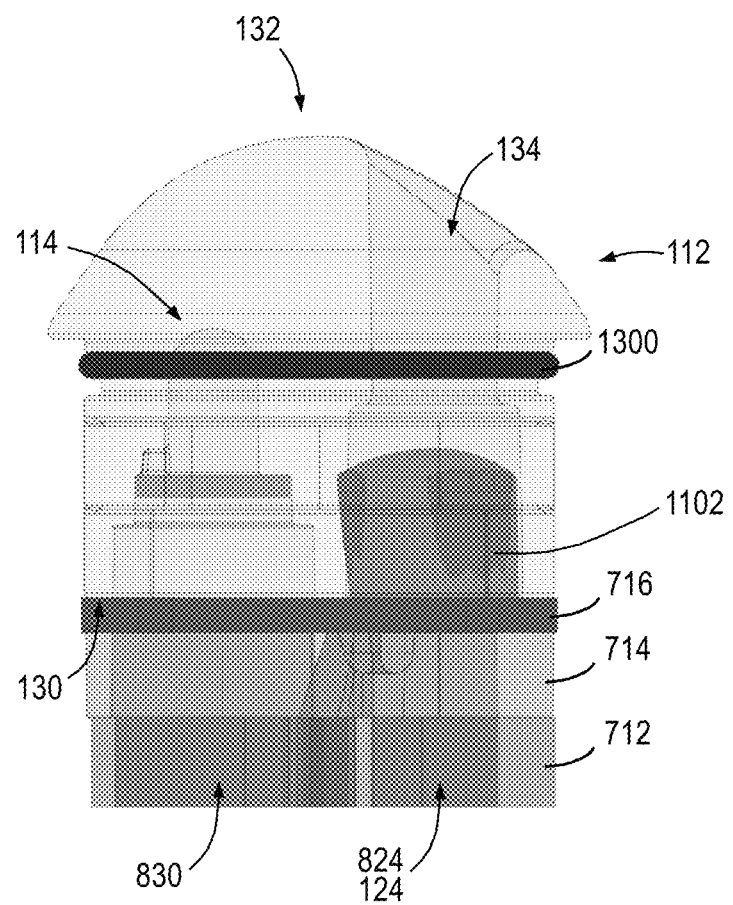
FIG. 13 is an enlarged view of a distal portion of the channel assembly, the bulb and an O-ring disposed around the bulb, in a direction C-C shown in FIG. 1, according to at least some embodiments.

FIG. 13 is an enlarged cross section view of a distal portion of the channel assembly 520, the bulb 112 and an O-ring 1300 that may be disposed around the bulb 112, in a direction C-C shown in FIG. 1, according to at least some embodiments.

Referring also now to FIGS. 8, 9A-9B, 10, 11A-11B, 12 and 13, in accordance with at least some embodiments, including but not limited to the illustrated embodiment, the sections, e.g., sections 702-716, of the channel assembly 520 may collectively define each of a plurality of channels. The plurality of channels may include: (i) a channel 824 that is a portion of the instrument channel 124 (and which may be aligned or at least substantially aligned with and in fluid communication with the instrument channel port 724), (ii) a plurality of flush channels including a first flush channel 826 and a second flush channel 828 (and which may be aligned or at least substantially aligned with and in fluid communication with the first flush port 726 and second flush port 728, respectively), and (iii) an imaging system channel 830 (and which may be aligned or at least substantially aligned with and in fluid communication with the imaging system port 730).

Unless stated otherwise, the term "collectively" means as a group. However, this does not require that every member of the group contribute equally thereto, or for that matter, that every member of the group contribute at all thereto.

The instrument channel 824 may be elongated and/or may extend along: (i) a major portion of a length of the channel assembly 520 and/or (ii) a major portion of the length of the port body 110.

Unless stated otherwise, the term "major portion" means a portion that is greater than 50%.

The plurality of flush channels, e.g., flush channels 826, 828, may each be elongated and/or may extend along: (i) a major portion of a length of the channel assembly 520, (ii) a major portion of the length of the port body 110, (iii) a major portion of a length of the instrument channel 824 and/or (iv) along a major portion of a length of the instrument channel 124 (as a whole).

In at least some embodiments, the plurality of flush channels may extend to or near the distal end of the channel assembly 520 and/or instrument port 110. In the illustrated embodiment, the plurality of flush channels, e.g., the first flush channel 826 and the second flush channel 828, each extend to the gasket and valve section 716.

In at least some embodiments, the channel 824 may be aligned or substantially aligned with one or more of the other portions of the instrument channel 124. In at least some embodiments, the plurality of flush channels, e.g., flush channels 826, 828, may each include a major portion that is parallel to, or at least substantially parallel to, a major portion of the channel 824 and/or the instrument channel 124.

Unless stated otherwise, the term "substantially parallel to" means does not intersect with along the length of the channel assembly 520 and/or the port body 110.

In at least some embodiments, each of the plurality of flush channels, e.g., flush channels 826, 828, includes a connection to and is in fluid communication with a distal end or other portion of the instrument channel 824, 124. In the illustrated embodiment, the connections are defined, at least in part, by the adapter and manifold section 714 and include: (i) a first channel 1026 (FIGS. 10, 17C) that is a portion of the first flush channel 826 and connects the first flush channel 826 to the instrument channel 824, 124, and (ii) a second channel 1028 (FIGS. 10, 17C) that is a portion of the second flush channel 828 and connects the second flush channel 828 to the instrument channel 824, 124. In the illustrated embodiment, the first channel 1026 and the second channel 1028 are bounded on the distal side, and thus defined at least in part, by a proximal side of the gasket and valve section 716.

The fluid line 158 of the flush system 150 may be connected to and in fluid communication with a proximal end or other portion of the channel 824, 124. In the illustrated embodiment, this connection is defined, at least in part, by the channel and side port section 706 and includes: (i) a port 734 (FIGS. 7, 8, 14A-14B, 15A-15B, 16, 17A) to receive a distal end of the fluid line 164, and (ii) a channel 834 (FIG. 8, 15A-15B) that connects the port 734 to the instrument channel 824, 124.

As stated above, in at least some embodiments, the flush system 150 further includes a valve, which may be a one-way valve.

In at least some embodiments, the valve is disposed to a distal side of the connections between the instrument channel 824, 124 and the plurality of flush channels, e.g., flush channels 826, 828, e.g., to prevent or otherwise limit fluid used by the flush system 150 from reaching the patient. In at least some embodiments, the valve may be disposed at or near the bulb channel. In the illustrated embodiment, this valve is defined by a valve 1100 (FIGS. 11A-11B) defined by the gasket and valve section 716.

As used herein, the term "one-way valve" means opens in response to pressure from one direction but not in response to pressure from the other direction. If the valve is forced or otherwise held open, e.g., by an instrument inserted therethrough, the valve may allow fluid flow in each direction.

As stated above, in at least some embodiments, including but not limited to the illustrated embodiment, the valve of the flush system 150 may be defined by the valve 1100 (FIGS. 11A-11B) of the gasket and valve section 716. In at least some embodiments, including but not limited to the illustrated embodiment, the gasket and valve section 716 may include a flexible base 1104, a flexible hollow body 1102, and the multi-leaflet valve 1100. In some embodiments, the gasket and valve 716 comprises or consists of a compliant material, such as silicone (e.g., 70 A durometer silicone).

The flexible hollow body 1102 may be configured to have a compressed state when the flexible hollow body 1102 is inserted (e.g., press fit) into a channel of a medical device. In the compressed state, the cross-sectional shape of the flexible hollow body 1102, in a plane parallel to the surface of the flexible base 1104, at least partially conforms to the cross-sectional shape of the channel. For example, when the flexible hollow body 1102 is inserted into a tubular channel, one or more portions of the flexible hollow body 1102 may be compressed and/or deformed inwardly. The cross-sectional shape of the flexible hollow body 1102 in the compressed state may be another irregular shape or it may be circular or annular to conform to the circular cross-sectional shape of the tubular channel. In another example, when the flexible hollow body 1102 is inserted into a channel that has an oval cross-sectional shape, the cross-sectional shape of the flexible hollow body 1102 in the compressed state may be an oval or an oval ring to conform to the cross-sectional shape of the channel. Inserting the flexible hollow body 1102 into a channel, such that the flexible hollow body 1102 is in a compressed state, may cause a wall of the flexible hollow body 1102 to exert an outward force against the channel wall. The outward force of the wall may cause the wall and the channel wall to be in direct physical contact with each other to secure or partially secure the flexible hollow body 1102 to the channel wall. In other embodiments, the multi-leaflet valve 1100 has more than 3 leaflets or only 2 leaflets.

The multi-leaflet valve 1100 may be configured to open when at least a minimum or threshold force is applied to the multi-leaflet valve 1100 in a first direction, for example when a surgical instrument is inserted through the channel 150 in the flexible hollow body 1102 from its proximal end to its distal end. When a surgical instrument is inserted through the multi-leaflet valve 1100, the leaflets exert an inward force towards the surgical instrument so that they close when the surgical instrument is removed. When the operating pressure differential across the multi-leaflet valve 1100 is lower than a minimum pressure differential, the multi-leaflet valve 1100 remains closed and a seal is maintained. On the proximal side of the multi-leaflet valve 1100, a first pressure may be applied when a fluid, such as saline, is introduced in the channel in the flexible hollow body, for example to flush the channel before a surgical instrument is inserted through the multi-leaflet valve 1100. A negative pressure may also be applied to one or more fluid return channels that is/are in fluid communication with the proximal end of the channel and with a vacuum source. On the distal side of the multi-leaflet valve 1100, a second pressure may be applied when it is exposed to bodily fluids, such as when the gasket 716 is inserted into a surgical site in a patient as a component of an instrument port. The operating pressure differential is the difference between the pressure on the proximal and distal sides of the multi-leaflet valve. In at least some embodiments, the multi-leaflet valve 1100 is configured such that the minimum pressure differential needed to open the multi-leaflet valve 1100 (e.g., the cracking pressure) is significantly greater than the typical or maximum operating pressure differential across the multi-leaflet valve 1100. In at least some embodiments, the compression of the flexible hollow body 1102 causes the channel wall to exert an inward force against the leaflets of the multi-leaflet valve 1100, which forces them closed and increases the minimum pressure differential needed to open the multi-leaflet valve 1100

As also stated above, in at least some embodiments, the flush system 150 further includes a seal. In at least some embodiments, the seal is disposed to a proximal side of the connection between the instrument channel 824 and the fluid line 164 to prevent or otherwise limit air from getting into the flush system 150 and/or to prevent or otherwise limit fluid used by the flush system 150 from leaking out the proximal end of the instrument channel 124. In the illustrated embodiment, the seal may be defined by the gasket 704 and may include a narrowed portion 844 (FIG. 8, 15A-15B, 17A, 18A-18B) of the instrument channel 824 that is configured to seal against an instrument, e.g., the instrument 102 or the instrument 104, inserted therein.

In at least some embodiments, the flush system 150 may operate as follows. When fluid is supplied to the fluid line 164 from the port 154 coupled to the fluid source 174, and suction is applied to the fluid line 162 from the port 152 coupled to the suction source 176, fluid is drawn through the fluid line 164 into the fluid line 512, through the fluid line 512 and into the port 734, through the port 734 into the channel 834, and through the channel 834 into the instrument channel 824, 124. The fluid flows through the instrument channel 824, 124 (in a gap between the inner walls of the channel 824, 124 and the instrument inserted therein). The fluid, which may carry emboli and/or debris removed from the instrument channel 124, is withdrawn from the instrument channel 824, 124 through the flush channels 826, 828 (including the connections 1026, 1028, respectively) into the ports 726, 728, respectively, through the ports 726, 728 into the fluid lines 506, 508, through the fluid lines 506, 508 into the fluid line 162, through the fluid line 162 into the port 152, and out of the instrument port 100 through the port 152.

In at least some embodiments, suction may alternatively be applied to port 154 and fluid line 158 and fluid may alternatively be supplied to the port 152 and fluid line 156. In such embodiments, the direction of fluid flow is a reverse of that described above. In some such embodiments, it may be desirable to swap the configurations of ports 152, 154 and to swap the configurations of valves 166, 170.

In at least some embodiments, one or more of the valves 166, 170 (and/or other valves) may be included and used to control when suction is applied to fluid line 162 and/or when fluid is supplied to fluid line 164.

In at least some embodiments, the valve 170 is manually opened (e.g., as described above) prior to a procedure and left open until the procedure is completed. The valve 166 is then manually opened (e.g., as described above) at the precise point(s) in time that flushing is desired. The valve 166 is then manually closed. After the procedure is completed, the valve 170 is manually closed.

As discussed, the flush system 150 may include a one-way valve. In at least some embodiments, the one-way valve opens responsive to a positive pressure applied to the valve from within the bulb channel 105, such as when pushed open during insertion of the instrument therethrough. During flushing of the instrument port, when a negative pressure (a suction) is applied to the one-way valve, the one-way valve remains closed, thus preventing emboli and debris carried by the flushing fluid from entering the patient's body. Additionally, this may prevent or reduce blood from the body from being drawn into the instrument channel by an applied suction. The one-way valve also remains closed when a positive pressure is applied to the valve from outside of the instrument port 100, such as when exposed to pressure in the heart, thus enabling the instrument port 100 to be used in high-pressure environments, such as in both atrial and ventricular applications, without aspiration of blood into the instrument channel 124 of the instrument port. In at least some embodiments, the one-way valve may be a check valve, which may be a compliant flexure that opens when pushed by the distal end of the instrument, remains sealed while the instrument is inserted therethrough, and seals when the instrument is removed. In at least some embodiments, the one-way valve may be a tricuspid valve.

The channel assembly 520 and instrument port 100 are further described below with respect to FIGS. 14A-14C, 15A-15C, 16, 17A-17C, 18A-18B and 19A-19C.

FIG. 14A is a cross sectional view in a direction A-A shown in FIGS. 7 and 9A-9B, of the channel assembly 520 and the bulb 112, according to at least some embodiments.

FIG. 14B is an enlarged cross section view in a direction A-A shown in FIGS. 7 and 9A-9B, of a proximal portion of the channel assembly 520 and the bulb 112, according to at least some embodiments.

FIG. 14C is an enlarged cross section view in a direction A-A shown in FIGS. 7 and 9A-9B, of a distal portion of the channel assembly 520 and the bulb 112, according to at least some embodiments.

FIG. 15A is a cross sectional view in a direction B-B shown in FIGS. 7 and 9A-9B, of the channel assembly 520 and the bulb 112, according to at least some embodiments.

FIG. 15B is an enlarged cross section view in a direction B-B shown in FIGS. 7 and 9A-9B, of a proximal portion of the channel assembly 520 and the bulb 112, according to at least some embodiments.

FIG. 15C is an enlarged cross section view in a direction B-B shown in FIGS. 7 and 9A-9B, of a distal portion of the channel assembly 520 and the bulb 112, according to at least some embodiments.

Figure 16:
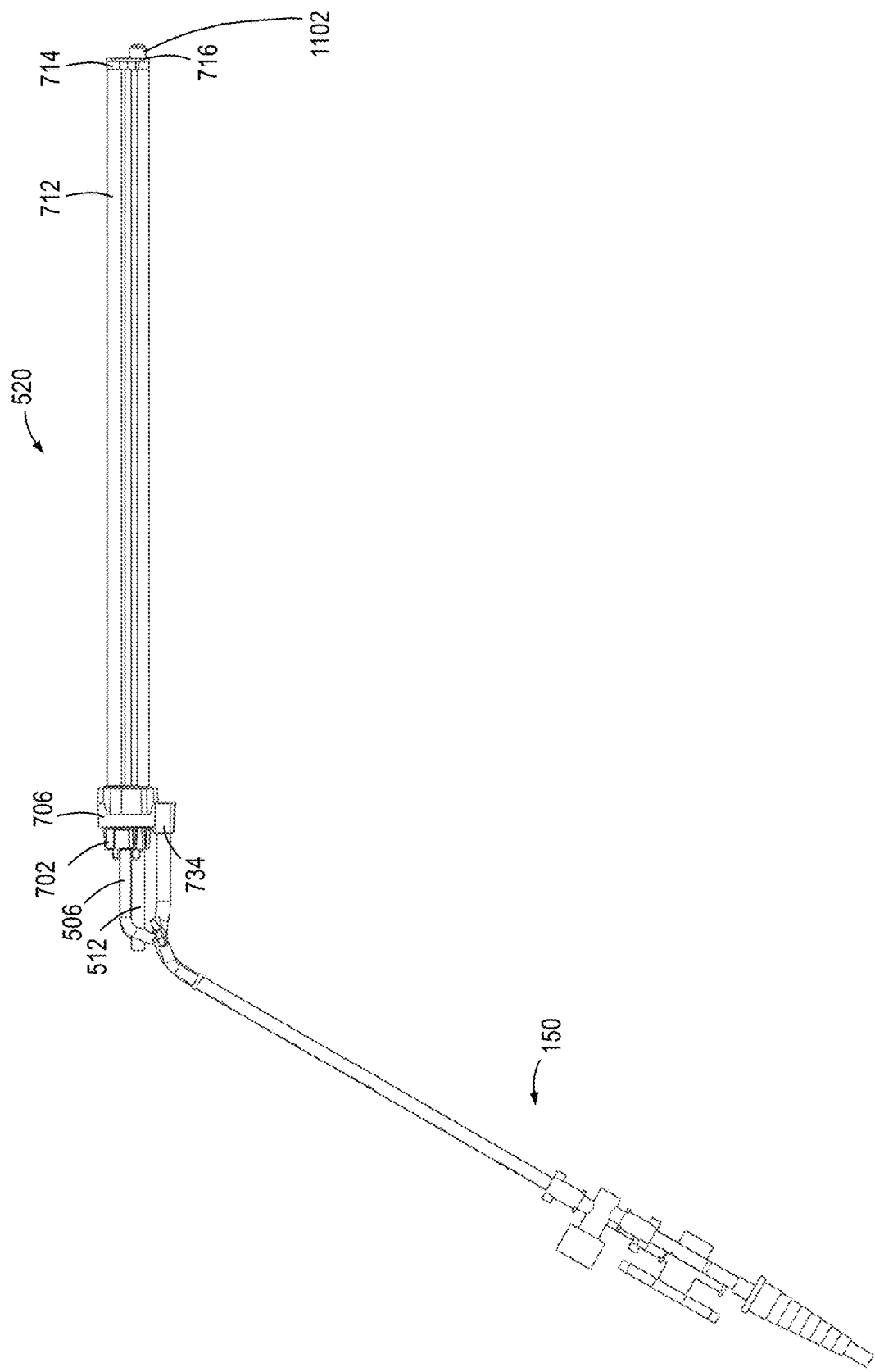
FIG. 16 is a side view of a portion of the channel assembly, fluid lines, and ports, according to at least some embodiments.

FIG. 16 is a side view of a portion of the channel assembly 520 and a portion of the flush system 150, according to at least some embodiments.

FIG. 17A is an enlarged proximal end view of a portion of the channel assembly 520, according to at least some embodiments.

FIG. 17B is an enlarged proximal end view of a portion of the channel assembly 520, according to at least some embodiments.

FIG. 17C is an enlarged proximal end view of a portion of the channel assembly 520, according to at least some embodiments.

Figure 18B:
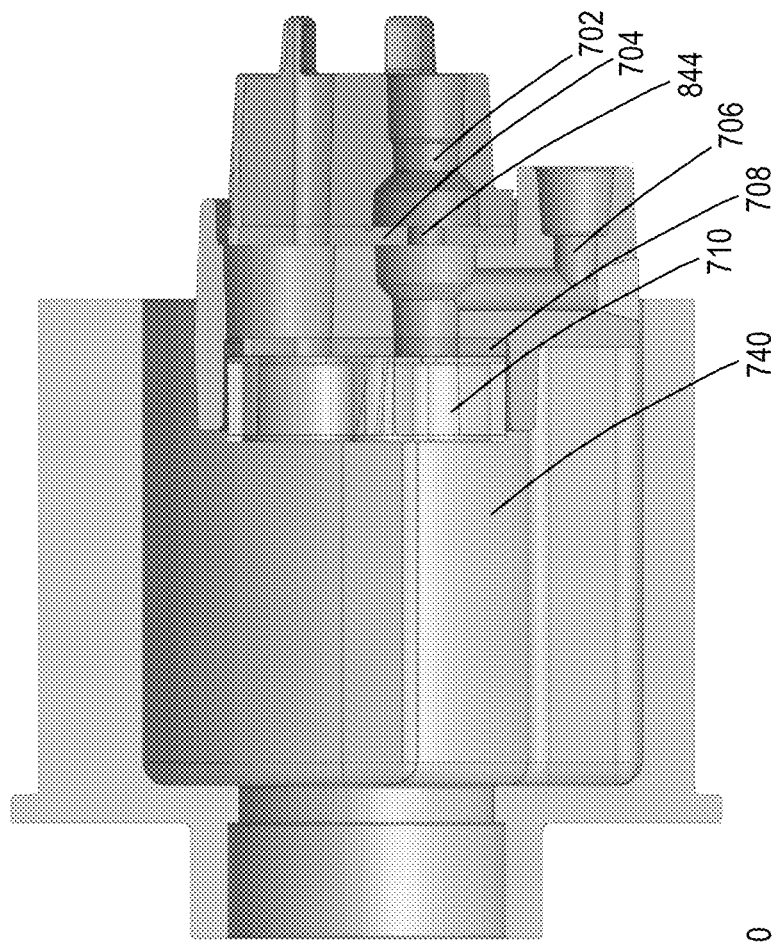
FIG. 18B is an enlarged cross section view in a direction B-B shown in FIG. 7 of the channel assembly, according to at least some embodiments.
Figure 18A:
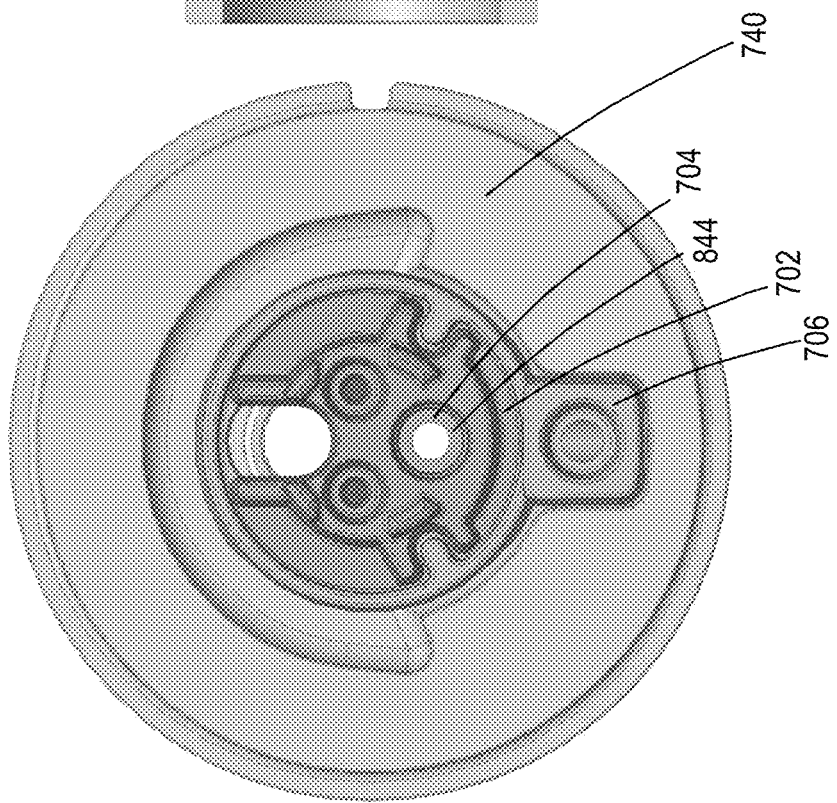
FIG. 18A is a proximal end view of the channel assembly, according to at least some embodiments.

FIG. 18A is a proximal end view of the channel assembly 520, according to at least some embodiments.

FIG. 18B is an enlarged cross section view in a direction B-B shown in FIG. 7 of the channel assembly 520, according to at least some embodiments.

Figure 19A:
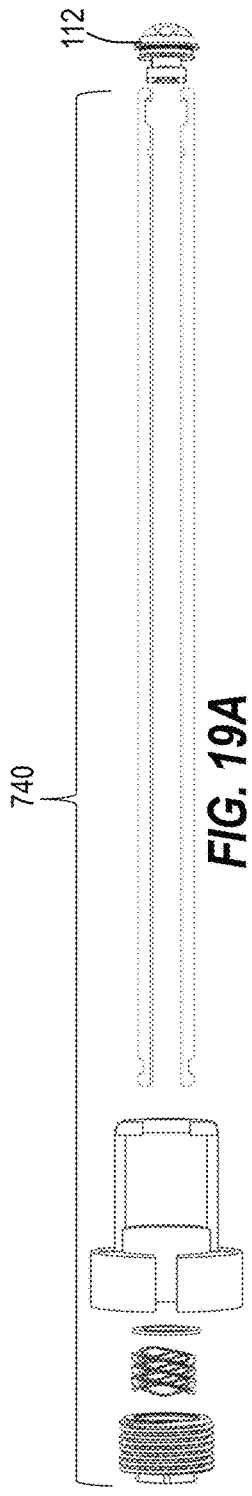
FIGS. 19A-19C are side views showing assembly of a retainer of the channel assembly, according to at least some embodiments.
Figure 19B:
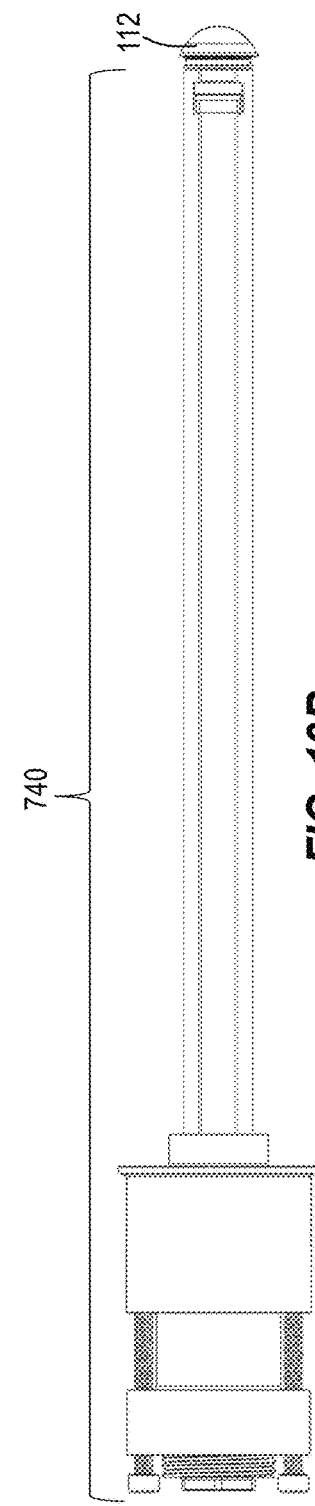
Figure 19C:
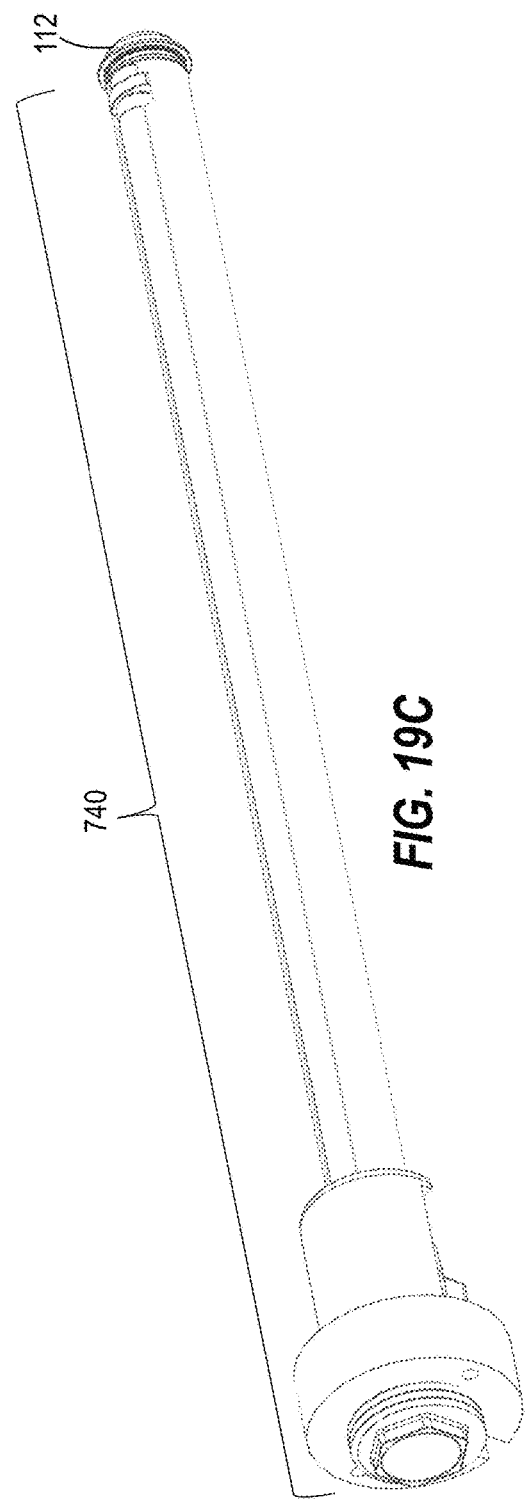

FIGS. 19A-19C are side views showing sequential assembly of the retainer assembly 740 of the channel assembly 520.

Referring also now to FIGS. 14A-14C, 15A-15C, 16, 17A-17C, 18A-18B and 19A-19C, in at least some embodiments, including but not limited to the illustrated embodiment, the sections, e.g., sections 702-716, of the channel assembly 520 and the bulb 112 are configured to be assembled together to form a linear array, sometimes referred to herein as a stack (which may be disposed about and/or extend along a longitudinal axis, e.g., longitudinal axis 131, and/or which may extend in a longitudinal direction, e.g., longitudinal direction 133), with a desired relative positioning of the sections, e.g., sections 702-716, and the bulb 112, within the linear array.

In at least some embodiments, two or more of the sections, e.g., sections 702-716, and the bulb 112 may be configured to provide at least a portion of the desired relative positioning. For example, in the illustrated embodiment, the channel and side port section 706 defines (i) a recessed seat 860 (FIG. 8) that is configured to receive the gasket 704 and the port section 702 and to provide relative positioning thereof in longitudinal and lateral directions, and (ii) a raised portion 862 (FIG. 8) that is configured to be received by channels 864, 866 (FIG. 8) defined by the gasket 704 and port section 702, respectively, to provide desired relative angular positioning between the sections 702-706. The gasket and valve section 716 may include a raised portion 1102 (FIGS. 11A-11B, 13, 15A-15B, 16) that is received by the bulb channel 134 to thereby provide desired relative positioning therebetween in longitudinal and/or lateral directions.

In at least some embodiments, including but not limited to the illustrated embodiment, the retainer assembly 740 of the channel assembly 520 may include: (i) laterally opposed side walls, which may provide or help provide relative positioning between two or more of the sections of the channel assembly 520 and bulb 112 and (ii) a tension or other type mechanism that may provide compression force in a longitudinal direction to retain the sections of the channel assembly 520 and the bulb 112 in a desired relative positioning.

In at least some embodiments, one or more of the adapter sections 710, 714 may be used to compensate for variance (between desired dimensions and actual dimensions) that may occur in the elongated channel section 712 as a result of, for example, manufacturing tolerances. In some other embodiments, any variance may be insignificant and/or separate adapters may not be employed. In some such embodiments, sections 710, 712, 714 may be fabricated as a single integral part. In some other embodiments, one of the sections 710, 714 may comprise a separate adapter and the other may be fabricated integral with the elongated channel section 712. In some other embodiments: (i) the adapter section 710 may not be needed and may not be included in the assembly and/or (2) the manifold section 714 (whether separate from or integral with the elongated channel section 712) may not need to be and may not be an adapter.

In at least some embodiments, including but not limited to the illustrated embodiment, the extended channel section 712 may be fabricated using extrusion and/or any other suitable process(s).

In at least some embodiments, the elongated channel section 712 and the manifold 714 may be fabricated as a single integral part using an extrusion or other suitable process(es) to define an elongated channel section and subsequent machining to define a manifold at a distal end of the elongated channel.

In at least some embodiments, including but not limited to the illustrated embodiment, the port section 702, the gasket 704, the side port section 706, the channel gasket 708, the channel adapter 710 (if included and if separate from elongated channel section 712), the manifold section 714 (with or without an adapter portion and if separate from the elongated channel section 712) and the gasket and valve section 716 may be fabricated using molding and/or any other suitable process(es).

In at least some embodiments, the channel 834 may include a portion that is transverse to the channel 824. Such portion may be created as part of a molding process that may be used to fabricate the side port section 706, by boring or any other suitable process(es). If an opening is created as a result of such process(es) and desired to seal, a plug 836 may be inserted to seal such opening.

As stated above, in at least some embodiments, a plurality of flush channels that are separate from the instrument channel and in fluid communication therewith, have less impact on a size (e.g., width) of the instrument port than if a single large flush channel is provided.

This is further discussed below with respect to FIG. 20.

Figure 20:
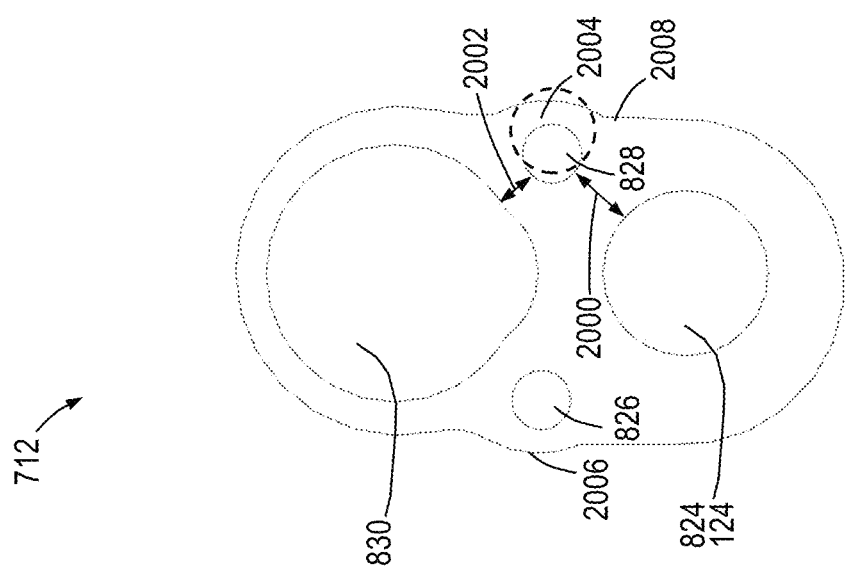
FIG. 20 is an end view of the elongated channel section, in accordance with some embodiments.

FIG. 20 is an end view of the elongated channel section 712, in accordance with some embodiments.

Referring to FIG. 20, as stated above, in accordance with at least some embodiments, the elongated channel section 712 includes the instrument channel 824, the imaging channel 830 and the plurality of flush channels 826, 828. The channels are positioned so as to provide (i) a first wall thickness 2000 between the flush channel 828 and the instrument channel 824, and (ii) a second wall thickness 2002 between the flush channel 828 and the imaging channel 830.

Shown in phantom is a single large flush channel 2004. The single large flush channel 2004 is shown positioned so as to provide a similar spacing from the instrument channel 826 and imaging channel 830.

As can be seen, the single large flush channel 2004 would not fit within the perimeter of the elongated channel section 712.

Thus, the impact of providing the plurality of flush channels 826, 828 is less than the impact of providing the single large flush channel 2004, which can be a space-saving advantage, especially in instruments designed for use in small surgical apertures.

In at least some embodiments, the first flush channel 826 (or at least a major portion thereof) and the second flush channel 828 (or at least a major portion thereof) may be disposed adjacent to, or otherwise toward, opposite sides of the elongated channel section 712, opposite sides of the channel assembly 520 and/or opposite sides of the port body 110.

In the illustrated embodiment, the first flush channel 826 is disposed toward and adjacent to a first side 2006 of the elongated channel section 712 (and toward a first side of the channel assembly and a first side of the port body 110). The second flush channel 828 is disposed toward and adjacent to a second side 2008 of the elongated channel section 712 (and toward a second side of the channel assembly 520 and a second side of the port body 110).

Unless stated otherwise, the term "toward a side" means closer to the side than to an opposite side thereof.

In at least some embodiments, the port body 110 may have any suitable configuration and is not limited to the embodiments above. In some embodiments, the port body 110 may include a plurality sections or segments (which may be the same as or different from the sections or segments described above)). Each section or segment may include the same or different material(s) as the other sections or segments. The segments/sections may be joined with an adhesive, a screw, or other device. In at least some embodiments, a fluid tight seal is not needed between the handle 120 and the shaft 122. In at least some embodiments, it may be preferably to form a fluid-tight seal between other adjacent segments/sections.

In at least some embodiments, the port body 110 may be constructed as a disposable component that is intended for a single-use application. In at least some embodiments, one or more portions of the port body 110 may be formed from, or may include polycarbonate, polyvinylidene fluoride, Kynar® polymer plastic, PVC, polypropylene, polyacetal, PEEK, or another polymer; silicone; silicone rubber stainless steel, glass, and/or other material(s). In at least some embodiments, the port body 110 may be formed from, or may include, a material that is ultrasound visible, such that the position of the instrument port 100 in the body of the patient may be visualized by ultrasound imaging. In at least some embodiments, such as when the port body 110 is formed from a material that is not ultrasound visible, one or more ultrasound visible markers may be attached to or included on the port body 110 to enable visualization of the position of the instrument port 100 by ultrasound imaging. Optionally, the port body 110 may be formed from or coated with a hydrophilic material, such as polyvinylidene fluoride (PVDF), P(VDF-trifluoroethylene), P(VDF-tetrafluoroethylene), polytetrafluoroethylene (PTFE), another hydrophilic material, or a combination of two or more of the foregoing, to facilitate flushing of air bubbles from the instrument channel 124.

In at least some embodiments, the imaging system 114 may be positioned (e.g., within the bulb 112) such that the opening of the bulb channel 134 and at least a portion of the distal face 132 of the bulb 112 fall within the field of view of the camera, thus enabling imaging of the surgical site, the instrument emerging from the bulb channel 134, and/or the interaction between the instrument and tissue or medical devices at the surgical site. In at least some embodiments, the bulb 112 may be designed such that there are few or no obstructions blocking the field of view of a camera of the imaging system 114. The camera of the imaging system 114 may be set back from the distal face 132 of the bulb 112 by an amount approximately equal to the focal distance of the camera. In at least some embodiments, the illumination source of the imaging system 114 may be positioned relative to the camera and to the distal face 132 of the bulb 112 such that the field of view of the camera is uniformly illuminated. Uniform illumination may help prevent the occurrence of shadows or dark spots that may limit the quality of the images acquired by the camera.

In at least some embodiments, the imaging system 114 may be fluidically isolated from the exterior of the instrument port 100 (e.g., from tissue and body fluids, such as blood, external to the instrument port 100), from the instrument channel 124 and the bulb channel 134, and from an instrument inserted into the instrument channel 124 and bulb channel 134. Thus, in at least some embodiments, the bulb 112 acts as an enclosure that fluidically isolates the components of the imaging system 114 from the exterior of the instrument port 100, from the instrument channel 124 and bulb channel 205 134, and from the instrument. Fluidically isolating the components of the imaging system 114 helps to prevent electrical signals from the imaging system from being carried to the surgical site by tissue, blood, or the instrument, thus helping to avoid unintended electrical stimulation of the surgical site. Unintended electrical stimulation may be particularly dangerous in cardiac procedures, in which unintended stimulation of the heart muscle may give rise to arrhythmias in the patient. Thus, the fluidic isolation is not only beneficial, but may also be important to prevent adverse health effects to the patient. Fluidically isolating the components of the imaging system 114 may also reduce the risk of infection during surgery since by reducing the number of components exposed to the surgical area. The present system also avoids or minimizes unwanted effects such as body fluids near the imaging (camera) device at the distal end of the system adversely affecting the viewing capability near the surgical site.

The bulb 112 may be designed to reduce internal reflection of light at its distal face 132, enabling the surgical site to be well illuminated. For instance, in at least some embodiments, the bulb 112 may be formed of a material having a refractive index similar to that of air, blood, or tissue, such that internal reflections at the distal face 132 of the bulb 112 are reduced. In at least some embodiments, the bulb 112 may comprise glass, clear crystal, resins such as acrylics or polyurethanes, or other materials with a refractive index sufficient to reduce internal reflections at the distal face 132 of the bulb 112. In addition, or in the alternative, the relative angle between the distal face 132 of the bulb 112 and the direction of illumination from the illumination source may be set to reduce internal reflections at the distal face 132 of the bulb 112. In addition, or in the alternative, internal reflections at the distal face 132 of the bulb 112 may be reduced by the presence of an anti-reflective coating on the inner surface of the bulb.

In at least some embodiments, to carry out a surgical procedure, the instrument port may be inserted into a patient's tissue, such as into tissue of the patient's heart, through an incision in the patient's skin and tissue, such that the distal end 132 of the bulb 112 is positioned at or near a surgical site. The proximal end of the instrument port 100 extends outside of the chest wall and incision site to enable an operator to manipulate the instrument port 100. The instrument port 100 may be anchored in place at the surgical site, such as by suturing the instrument port 100 to the patient's tissue. An instrument may be inserted through the instrument channel 112 and the bulb channel 134, emerging from the distal opening of the bulb channel 134 on the distal end 132 of the bulb 112. The instrument port 100 may be positioned within the body of the patient such that the instrument may access the surgical site. The imaging system 114 may be positioned to be able to acquire images of the instrument emerging from the opening of the bulb channel 134, images of the surgical site, and/or images of the interaction between the instrument and the surgical site during the surgical procedure.

The instrument channel 124 and bulb channel 134 may be sized to accept standard instruments, such as, for example, but not limited to dissectors, graspers, scissors, needle holders, fan retractors, cautery instruments, insufflation needles, forceps, or other types of instruments. In at least some embodiments, the instrument channel 124 and the bulb channel 134 may each have a diameter of about 2 mm to about 6 mm, such as about 2 mm, about 3 mm, about 4 mm, about 5 mm, about 6 mm, or any value or range therebetween. As used herein, "about" means plus or minus 10% of the relevant value. In at least some examples, the instrument port 100 may include multiple instrument channels 124 and corresponding bulb channels 134 such that multiple surgical instruments may be inserted into the instrument port 100 simultaneously or sequentially. The multiple instrument channels and bulb channels may each have the same diameter or may each have different diameters. In at least some embodiments, each instrument channel 124 and corresponding bulb channel 134 (e.g., when there are multiple channels) may have the same or about the same diameter.

In at least some embodiments, a camera of the imaging system 114 may be a high-resolution camera, such as a camera with millimeter-level resolution or sub-millimeter-level resolution. In at least some embodiments, the camera may be a complementary metal-oxide semiconductor (CMOS) camera, a charge-coupled device (CCD) camera, or another type of camera. The camera may have a diameter of 5 mm or less. In at least some embodiments, the camera may comprise ⅛ Color CMOS CAMERA Module (Misumi Electronics Corp., Taiwan), Medigus Micro ScoutCam™ 1.2 system (Omer, Israel), and AWAIBA NanEye image sensor (CMOSIS AMERICA LLC, Raleigh, NC, USA). In at least some embodiments, the camera may capture still and/or moving images (e.g., as a video camera).

In at least some embodiments, an illumination source of the imaging system 114 may emit visible light (e.g., white light or light of a specific wavelength or range of wavelengths), near-infrared light, and/or ultraviolet light. In at least some embodiments, the illumination source may emit visible light between 400 nm and 700 nm, infrared light between 1400 nm and 3000 nm, near infrared light between 700 nm and 1400 nm, and/or ultraviolet light between 280 nm and 400 nm. In at least some embodiments, the illumination source may include or may be optically coupled to (e.g., via a light guide) one or more light emitting diodes (LEDs) capable of emitting the desired wavelength(s) or wavelength range(s).

In at least some embodiments, the bulb 112 may be formed of a biocompatible material that is optically transparent to light used by the imaging system 114, such as visible light, infrared light, or ultraviolet light. An optically transparent material is a material that is at least partially transparent with respective to one or more wavelengths of light. For example, the bulb 112 may be formed of acrylic, silicone, polycarbonate, polypropylene, polyacetal, polyether ether ketone (PEEK) and/or another material. In at least some embodiments, the lighting employed may have wavelengths in the visible spectrum, for example between 400 nm and 700 nm. In at least some other embodiments, illumination using infrared or near-infrared (IR) wavelengths, e.g., between 700 nm and 900 nm, or even up to 2000 nm may be used. In yet some other embodiments, a quartz optical component may be employed that permits ultra-violet illumination, e.g., using wavelengths between 250 nm and 400 nm. In at least some embodiments, the bulb 112 may be fabricated by injection molding, casting, extrusion, three-dimensional (3-D) printing, or another fabrication process.

In at least some embodiments, during use, the instrument port 100 is positioned such that the distal face 132 of the bulb 112 comes into contact with tissue or a medical device (e.g., a patch) at the surgical site. In at least some embodiments, contact between the distal face 132 of the bulb 112 and the tissue or medical device at the surgical site displaces blood from between the distal face 132 of the bulb 112 and the surgical site, creating a path between the imaging system 114 and the surgical site that is optically clear to visible light. To facilitate displacement of blood, the bulb 112 may be formed of a slightly deformable material, thus enabling the bulb 112 to conform or at least better conform to the shape of the tissue or medical device at the surgical site.

The shape of the distal face 132 of the bulb 112 may be selected based on characteristics of the surgical site where the instrument port 100 is to be used, e.g., based on characteristics of the tissue or medical device at the surgical site where the bulb 112 is to be used. In at least some embodiments, the distal face 132 of the bulb 112 may be rounded such that the bulb 112 has a hemispherical shape. A hemispherical bulb 112 with a rounded distal face 132 may be used, for instance, to contact soft tissue, such as in cardiac applications. In at least some embodiments, the distal face 132 of the bulb 112 may be flat, for instance, for use in contacting stiffer tissue such as muscle fascia, cartilage, bone, or in contacting soft tissue containing calcium deposition such as aortic or mitral valve annulus. In at least some embodiments, such as when the bulb 112 is to be used to contact multiple types of tissue with varying characteristics, the distal face 132 of the bulb 112 may have both a rounded portion and a flat portion.

In at least some embodiments, the camera and the illumination source may be powered by a battery (not shown), which may be housed at or near the distal end of the port body 110, or housed in the bulb 112. In at least some embodiments, the camera and the illumination source may be configured for wireless power transmission, wireless data transmission, or both. In at least some embodiments, the data collected by the camera may be transmitted in real time (e.g., with little or no delay between acquisition and transmission) for viewing by the operator of the instrument port 100 such that the operator may conduct the surgical procedure with guidance from the images.

In at least some embodiments, a fluid-tight seal between the bulb 112 and the port body 110 helps to prevent fluid from reaching the imaging system 114 and helps prevent electrical signals from the imaging system from reaching tissue, blood, or the instrument. In at least some embodiments, a fluid-tight seal between the bulb 112 and the port body 110 may comprise a gasket seal, a pressure-fit seal, a medical grade adhesive, an O-ring attachment, and/or another type of sealing mechanism, or combination of two or more of the foregoing. In at least some embodiments, a fluid tight seal may be constructed to withstand the fluid pressure present in the chambers of the heart, such as pressures of up to 150 mmHg or pressures as low as 3 mmHg. Some embodiments permit operation, especially during transients, in a pressure range up to 220 mmHg or as low as −5 mmHg. In at least some embodiments, the bulb 112 may be removably attached to the port body 110 or the bulb 112 may be permanently attached to the port body 110.

In at least some embodiments, the geometry of the bulb 112 may be optimized for use with a particular wavelength or range of wavelengths of light.

In at least some embodiments, the instrument port 100 may be a single-use, disposable surgical device such that the instrument channel does not need to be easily cleaned and sterilized for reuse. In at least some embodiments, the port body of the instrument port 100 may be a reusable device and the bulb 112 may be a single-use, disposable device that may be removably attached to the port body by a reversible closing mechanism, such as a pressure-fit seal, an O-ring attachment, or another closing mechanism. In at least some embodiments, an imaging system may be embedded in the bulb 112 and may be disposable along with the bulb 112. In at least some examples, the imaging system may be reusable and may be cleaned and sterilized and inserted into each disposable bulb.

In at least some embodiments, the instrument port 100 may be used to perform beating heart or other cardiac procedures, which may include but are not limited to, closure of heart defects, such as septal defects, heart valve annuloplasty, and other procedures. In at least some embodiments, the instrument port 100 may provide high quality imaging of the surgical procedure, and may thereby enable complex surgical procedures to be carried out with a high degree of precision.

In at least some embodiments, the instrument port 100 may be used to perform a patent foramen ovale (PFO) closure procedure. In such a procedure, a patch is applied to a septum of a patient's heart to close a hole in the septum. An incision may be made through an atrial or ventricular wall of a patient's heart and secured with a suture, such as a purse-string suture. The distal end of the instrument port 100 may be inserted through the incision such that the distal face of the bulb 112 is positioned near or in contact with the septum of the patient's heart. The proximal end of the instrument port 100 remains outside the patient's body, enabling an operator of the instrument port 100 to adjust the position of the instrument port 100 and to manipulate an instrument inserted into the instrument port 100. After the instrument port 100 is positioned as desired, it may be secured in place, e.g., using a purse-string suture, to prevent or otherwise limit blood leakage during the procedure.

In at least some embodiments, after the instrument port 100 is secured, a first instrument, such as graspers, scissors, a tissue anchor deployment device, a tissue stapler, a needle holder, or another type of instrument, may be inserted through the instrument port to the surgical site and used to place the patch over the hole in the septum. In at least some embodiments, the instrument port 100 includes an imaging system 114 to image the first instrument as the instrument emerges from the bulb channel and manipulates the patch, providing valuable feedback to the operator of the instrument port 100 about the condition of the patient's septum and/or the relative positions of the patch and the septum. After the patch has been placed in a desired location, the first instrument may be withdrawn and a second instrument, such as, for example, an anchor deployment device, a stapler, a needle holder (e.g., RD80), a suturing device (e.g., SR5 from LSI Solutions® LLC), or another type of instrument, may be inserted through the instrument port 100 to the surgical site. In an example, the instrument port 100 may be used with a tissue tacking system and/or optically-guided surgical devices. The second instrument may be used to anchor the patch onto the septum, e.g., by stitching the patch onto the septum, adhering the patch using a medical grade adhesive, or attaching the patch in another way. The imaging system may be used image the second instrument as the instrument emerges from the bulb channel and interacts with the patch, providing information to the operator of the instrument port about the relative positions of the patch and the instrument. After the procedure is complete, the second instrument may be withdrawn from the instrument port and the instrument port may be withdrawn from the incision.

In operation, one or more images of a surgical site and/or of the distal end of the instrument port may be acquired using an imaging system of the instrument port. In at least some embodiments, the location of the instrument and/or the instrument port may be adjusted based on acquired image(s).

In at least some embodiments, the instrument port 100 may be employed in other surgical procedures. In at least some embodiments, other methods may be employed in the above described surgical procedure and/or any other surgical procedure in which the instrument port 100 is employed.

Some aspects may be embodied as one or more methods. The acts performed as part of the method may be ordered in any suitable way.

It should be understood that the features disclosed herein may be used in any combination or configuration. Thus, in at least some embodiments, any one or more of the embodiments (or feature(s) thereof) disclosed herein may be used in association with any other embodiment(s) (or feature(s) thereof) disclosed herein. Similarly, in at least some embodiments, any one or more of the features disclosed herein may be used without any one or more other feature disclosed herein.

Unless stated otherwise, terms such as, for example, "comprises," "has," "includes," and all forms thereof, are considered open-ended, so as not to preclude additional elements and/or features.

Also, unless stated otherwise, terms such as, for example, "a," "one," "first," are considered open-ended, and do not mean "only a", "only one" or "only a first", respectively.

Also, unless stated otherwise, the term "first" does not, by itself, require that there also be a "second."

Also, unless stated otherwise, the phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Elements other than those specifically identified by the "and/or" clause may optionally be present, whether related or unrelated to those elements specifically identified. Thus, as a non-limiting example, a reference to "A and/or B", when used in conjunction with open-ended language such as "comprising" may refer, in one embodiment, to A only (optionally including elements other than B); in another embodiment, to B only (optionally including elements other than A); in yet another embodiment, to both A and B (optionally including other elements); etc.

The present invention should therefore not be considered limited to the particular embodiments described above. Various modifications, equivalent processes, as well as numerous structures to which the present invention may be applicable, will be readily apparent to those skilled in the art to which the present invention is directed upon review of the present disclosure.

In the foregoing specification, certain aspects have been described with reference to specific embodiments. However, one of ordinary skill in the art appreciates that various modifications and changes may be made without departing from the scope of the present invention as set forth in the claims below. Accordingly, the specification and figures are to be regarded in an illustrative rather than a restrictive sense, and all such modifications are intended to be included within the scope of present invention.

What is claimed is:

1. An instrument port for introducing an instrument into a surgical site, the instrument port comprising:
   a port body including:
      an instrument channel extending through the port body, and
      first and second fluid flush channels each separate from one another and spaced laterally apart from the instrument channel, each extending along a major portion of the port body and in fluidic communication with the instrument channel, wherein the first and second fluid flush channels each comprise:

a first portion that extends parallel to the instrument channel and spaced alongside and laterally apart from the instrument channel, and a second portion that extends transverse to the instrument channel and connects to the instrument channel, wherein outer boundaries of the first portions of each of the first and second fluid flush channels define entirely separate interior volumes (i) from one another and (ii) from an interior volume defined by an outer boundary of the instrument channel, and wherein the first portions of each of the first and second fluid flush channels are arranged adjacent to opposite sides of the port body;

a bulb comprising a bulb channel extending through the bulb, the bulb channel aligned with the instrument channel, wherein the bulb channel and instrument channel are configured to receive the instrument;

a port connectable to a source of partial vacuum; and a valve in fluid communication between the port and either or both of the first and second fluid flush channels or between the port and the instrument.

2. The instrument port of claim 1, comprising:

a second port connectable to a source of fluid; and a second valve in fluid communication between the second port and the instrument channel or between the second port and either or both of the first and second fluid flush channel.

3. The instrument port of claim 1, wherein the second portion of each of the first and second fluid flush channels is defined at least in part by a manifold.

4. The instrument port of claim 1, wherein the instrument port comprises a channel assembly having a plurality of sections that are assembled in a linear array and collectively define at least a portion of the instrument channel and the first and second fluid flush channels.

5. The instrument port of claim 1, wherein the port body includes an imaging system channel separate from the instrument channel and the first and second fluid flush channels and extending along the major portion of the port body.

6. The instrument port of claim 1 comprising an imaging system comprising a camera and an illumination source, the illumination source configured to generate light having a first wavelength, wherein the bulb is at least partially optically transparent to the first wavelength of the light.

7. An instrument port for introducing an instrument into a surgical site, the instrument port comprising:

a port body including:
an instrument channel extending through the port body, and
first and second fluid flush channels each separate from one another and spaced alongside and laterally apart from the instrument channel, each extending parallel to the instrument channel along a major portion of the port body and in fluidic communication with the instrument channel;

a channel assembly having a plurality of sections that are assembled in a linear array; and a bulb at a distal end of the channel assembly, wherein the plurality of sections includes, in order in a distal direction, a port section, a first channel gasket, a channel and side port section, a second channel gasket and an elongated channel section that collectively define at least a portion of the instrument channel and the first and second fluid flush channels, and wherein the port section comprises a first port for a first external fluid line, wherein the channel and side port section comprises a second port for a second external fluid line, and wherein fluidic connections between the first and second fluid flush channels and the instrument channel are located at positions that are proximal with respect to the bulb.

8. The instrument port of claim 7, wherein the elongated channel section has a first side that extends along a major portion of the channel assembly and a second side that is opposite the first side and extends along the major portion of the channel assembly, wherein a major portion of the first fluid flush channel is disposed adjacent to the first side of the elongated channel section, and wherein a major portion of the second fluid flush channel is disposed adjacent to the second side of the elongated channel section that is opposite the first side of the elongated channel section.

9. The instrument port of claim 7, wherein the plurality of sections comprises an adapter section disposed between the second channel gasket and the elongated channel section.

10. The instrument port of claim 7, wherein the plurality of sections comprises an adapter and manifold section disposed on a distal side of the elongated channel section.

11. The instrument port of claim 10, wherein the adapter and manifold section connects the first and second fluid flush channels to the instrument channel.

12. The instrument port of claim 7, wherein:
the port section comprises a quad port section,
the first channel gasket comprises a first quad channel gasket,
the channel and side port section comprises a quad channel and side port section,
the second channel gasket comprises a second quad channel gasket, and
the elongated channel section comprises an elongated quad channel section.

13. The instrument port of claim 12, wherein the elongated quad channel section comprises an elongated quad channel extrusion.

14. The instrument port of claim 12, wherein the elongated quad channel section includes a manifold at a distal end of the elongated quad channel section.

15. The instrument port of claim 14, wherein the manifold and the elongated quad channel section are an integral part.

16. An instrument port for introducing an instrument into a surgical site, the instrument port comprising:

a port body including:
an instrument channel extending through the port body, and
first and second fluid flush channels each separate from one another and disposed laterally away from the instrument channel, each extending along a major portion of the port body and in fluidic communication with the instrument channel;

a bulb comprising a bulb channel extending through the bulb, the bulb channel aligned with the instrument channel, wherein the bulb channel and instrument channel are configured to receive the instrument;

a gasket that defines a first instrument channel hole and first and second fluid flush channel holes, the first instrument channel hole aligned with the instrument channel and the first and second fluid flush channel holes aligned with the first and second fluid flush channels, respectively; and a manifold body that defines a second instrument channel hole that is aligned with the instrument channel and the first instrument channel hole, the manifold body disposed between the gasket and the bulb, wherein the bulb channel is aligned with the first and second instrument channel holes, and wherein the first and second instrument channel holes are configured to receive the instrument, and wherein first and second manifold channels are defined in the manifold body, the first and second manifold channels fluidly coupling the first and second fluid flush channel holes, respectively, to the second instrument channel hole.

17. The instrument port of claim 16, wherein the manifold body is an integral part.

18. The instrument port of claim 16, wherein the first and second manifold channels are defined at least partially by a proximal side of the manifold body.

* * * * *